United States Patent
Xu et al.

(10) Patent No.: US 10,501,443 B2
(45) Date of Patent: Dec. 10, 2019

(54) PYRIDONE COMPOUND AS C-MET INHIBITOR

(71) Applicant: FUJIAN COSUNTER PHARMACEUTICAL CO., LTD., Ningde, Fujian (CN)

(72) Inventors: Xiongbin Xu, Shanghai (CN); Gang Li, Shanghai (CN); Charles Z. Ding, Shanghai (CN); Lihong Hu, Shanghai (CN); Guoping Hu, Shanghai (CN); Jian Li, Shanghai (CN); Shuhui Chen, Shanghai (CN); Zhigang Chi, Shanghai (CN); Kun Wang, Shanghai (CN)

(73) Assignee: FUJIAN COSUNTER PHARMACEUTICAL CO., LTD., Ningde, Fujian (CN)

( * ) Notice: Subject to any disclaimer, the term of this patent is extended or adjusted under 35 U.S.C. 154(b) by 0 days.

(21) Appl. No.: 16/343,387

(22) PCT Filed: Oct. 27, 2017

(86) PCT No.: PCT/CN2017/107964
§ 371 (c)(1),
(2) Date: Apr. 18, 2019

(87) PCT Pub. No.: WO2018/077227
PCT Pub. Date: May 3, 2018

(65) Prior Publication Data
US 2019/0248763 A1    Aug. 15, 2019

(30) Foreign Application Priority Data
Oct. 27, 2016    (CN) .......................... 2016 1 0954377

(51) Int. Cl.
C07D 401/14    (2006.01)
A61P 35/00     (2006.01)
C07D 413/14    (2006.01)
C07D 417/14    (2006.01)
C07D 403/14    (2006.01)

(52) U.S. Cl.
CPC ............ C07D 401/14 (2013.01); A61P 35/00 (2018.01); C07D 403/14 (2013.01); C07D 413/14 (2013.01); C07D 417/14 (2013.01)

(58) Field of Classification Search
CPC .. C07D 401/14; C07D 403/14; C07D 413/14; C07D 417/14
See application file for complete search history.

(56) References Cited

U.S. PATENT DOCUMENTS

| 2007/0208046 A1 | 9/2007  | Otake et al.  |
| 2010/0234354 A1 | 9/2010  | Dorsch et al. |
| 2014/0329797 A1 | 11/2014 | Harter et al. |

FOREIGN PATENT DOCUMENTS

| CN | 1930126 A     | 3/2007  |
| CN | 101743241 A   | 6/2010  |
| CN | 104144925 A   | 11/2014 |
| WO | 0202519 A2    | 1/2002  |
| WO | 2009006959 A1 | 1/2009  |

OTHER PUBLICATIONS

Berge et al, "Pharmaceutical Salts", Journal of Pharmaceutical Science 66: 1-19 (1977).
Remington: The Science and Practice of Pharmacy, 21st Ed, Lippincott, Williams & Wilkins (2005).
International Search Report of PCT/CN2017/107964 dated Jan. 26, 2018.
Written Opinion of PCT/CN2017/107964 dated Jan. 26, 2018.
The first Office Action issued in the counterpart Chinese patent application No. 201780036464.X dated May 17, 2019.

*Primary Examiner* — Noble E Jarrell
(74) *Attorney, Agent, or Firm* — Foley & Lardner LLP

(57) ABSTRACT

Disclosed in the present invention is a type of pyridone compounds as c-met inhibitors, and specifically disclosed is a compound as shown in formula (I) or a pharmaceutically acceptable salt thereof.

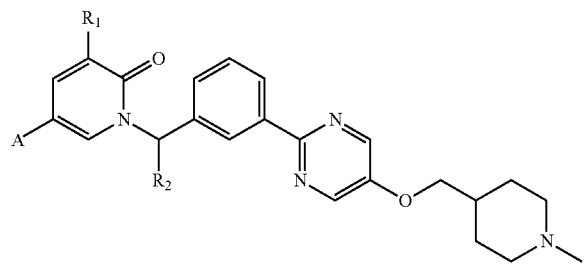

(I)

17 Claims, No Drawings

PYRIDONE COMPOUND AS C-MET INHIBITOR

FIELD OF INVENTION

The present invention relates to a class of pyridone compounds as c-Met inhibitor, specifically disclosed is a compound represented by formula (I) or a pharmaceutically acceptable salt thereof.

PRIOR ARTS

The c-Met encoded by proto-oncogene Met is a receptor tyrosine kinase with high binding belonging to RON subgroup. It is the only known receptor for scattering factor or hepatocyte growth factor (HGF). The c-Met protein is a disulfide-linked heterodimer composed of 50 kD α subunit and a 145 kD β subunit, which can be divided into extracellular domain and intracellular domain. The extracellular domain contains three structural domains with different functionality: N-terminal ligand bonding domain (SEMA region) covering the entire a chain and partially 0 chain, cystine enrichment domain with four conserved disulfide bonds, and immunoglobulin-like domain. The intracellular domain also consists of three regulatory domains: juxtamenbrane domain with Tyr1003 phosphorylation site, tyrosine kinase catalytic domain with Tyr1234 and Tyr1235 phosphorylation sites, and C-terminal multifunctional binding domain with Tyr1349 and Tyr1356 binding tyrosine.

HGF induces phosphorylation of c-Met by binding to its extracellular domain, and recruits a variety of interstitial factors such as GAB1 (growth factor receptor binding protein-1) and GAB2 (growth factor receptor binding protein-2) in the C-terminal multifunctional domain, which further attracts molecules such as SHP2. PI3K and others to bind here, hence activating RAS/MAPK, PI3K/AKT, JAK/STAT pathways etc., thereby regulating the growth, migration, proliferation and survival of cells. Abnormal action of the c-Met pathway would lead to tumorigenesis and metastasis, as abnormal high expression of c-Met was found in various human malignancies such as bladder cancer, gastric cancer, lung cancer and breast cancer. Besides, c-Met is also associated with tumor drug resistance to multiple kinase inhibitors.

The interaction between c-Met and various membrane receptors (crosstalk) constitutes a complex network system. Crosstalk between c-Met and adhesion receptor CD44 amplifies the response of signal peptide: crosstalk between c-Met and the brain protein receptor activates c-Met level of independent ligand HGF, and then enhances the invasion effect; crosstalk between c-Met and the pro-apoptotic receptor FAS accelerates apoptosis; crosstalks between c-Met and various receptor tyrosine kinases such as EGFR. VEGFR regulate the activation between each other, thus the angiogenesis process is affected. Crosstalk between c-Met and these membrane receptors promotes tumorigenesis, metastasis and induces drug resistance.

Transcription factor HIF-1α is a major regulator of tumor cells adapting to hypoxic environmental stress. VEGFR inhibitors cause tumor hypoxia in the early stage of treatment. Under hypoxic environment, HIF-1α up-regulates c-Met level, the increase of c-Met concentration thus promotes the tumor cells metastasis, generates regional expansion or metastasis of the tumors, leads the tumors to escape from the oxygen-deficient environment and then build a cloning system that more invasive and with stronger growing ability. Drug resistance of tumors to EGFR inhibitors might be related to the up-regulation of ligand HGF levels. c-Met augmentation was detected in 4%-20% patients with non-small cell lung cancer resistant to Gefitinib and Erlotinib, HGF develop resistance to EGFR kinase inhibitors by using GAB1 to regulate PI3K/AKT and ERK pathway. In mutated BRAF melanoma cell lines, researchers found that the augmentation of HGF would resist the effect of BRAF inhibitor Ramurafenib. Thus, the crosstalk between c-Met and membrane receptors induces resistance to kinase target therapy.

At present, there are a large amount of anti-tumor drugs on the market, such as alkylating agent drugs, anti-metabolite drugs, anti-tumor antibiotics and immunomodulators etc., but most of them are intolerant due to their high toxicity. With the in-depth study of tumor molecular biology, the molecular mechanism of tumorigenesis and development has been revealed more and more clearly, and molecular targeted therapy for a variety of malignant tumors has attracted extensive attention. Molecular targeted drugs are highly selective and broad-spectrum effective, they are safer comparing to cytotoxic chemotherapeutic drugs, thus indicating a new direction for development in the field of cancer treatment.

There are currently two kinds of anti-tumor drugs targeting at c-Met pathway: one is monoclonal antibody against HGF or c-Met; the other is small molecule inhibitor against c-Met. The small molecule inhibitors that already entered clinical research or under research include PF-2341066, EMD-1214063, XL-184 and ARQ-197 etc.

Among them, Tepotinib (EMDI214063) (WO2009006959, publication date 2009 Jan. 15) has the best antineoplastic activity, it has great inhibitory effect on a variety of c-Met overexpressed tumor cells (c-Met enzyme activity $IC_{50}$=3.67 nM. MHCC97H cell $IC_{50}$=6.2 nM), which has entered the stage of clinical research phase II.

However, although Tepotinib (EMDI214063) has a high selectivity, it has disadvantage of low metabolic stability and high clearance rate in vivo. Therefore, metabolically stable c-Met inhibitors are urgently needed to compensate for the deficiency.

Content of the Present Invention

The present invention provides a compound represented by formula (I) or a pharmaceutically acceptable salt thereof,

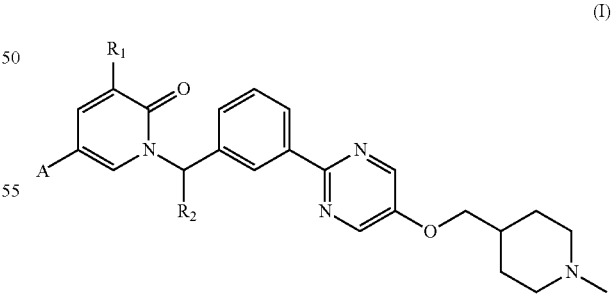

$R_1$ is selected from H or F;
$R_2$ is selected from H or $CH_3$;
while $R_2$ is not H, the configuration of the carbon atom bonded to $R_2$ is R or S;
A is selected from the group consisting of phenyl, pyridyl, pyrazolyl, isoxazolyl, isothiazolyl and thiazolyl, each of which is optionally substituted by 1, 2 or 3 $R_3$;

$R_3$ is selected from CN, halogen, C(=O)NH$_2$, or is selected from the group consisting of $C_{1-6}$ alkyl, $C_{1-6}$ heteroalkyl, and $C_{3-6}$ cycloalkyl, each of which is optionally substituted by 1, 2 or 3 $R_0$;

$R_0$ is selected from F, Cl, Br, I, OH, CN, NH$_2$, C(=O)NH$_2$, or is selected from the group consisting of $C_{1-3}$ alkyl and $C_{1-3}$ heteroalkyl, each of which is optionally substituted by 1, 2 or 3 R';

R' is selected from F, Cl, Br, I, CN, OH, NH$_2$, CH$_3$, CH$_3$CH$_2$, CF$_3$, CHF$_2$ or CH$_2$F.

The "hetero" in the $C_{1-3}$ heteroalkyl or $C_{1-6}$ heteroalkyl is selected from the group consisting of —O—, —C(=O)NR'—, —C(=O)NH—, —NR'—, and —NH—;

in any of the above cases, the number of the heteroatom or the heteroatomic group is independently selected from 1, 2 or 3.

In some embodiments of the present invention, $R_0$ is selected from F, Cl, Br, I, OH, CN, NH$_2$, C(=O)NH$_2$, CH$_3$, CH$_3$CH$_2$, CFA, CHF$_2$, CH$_2$F, NH$_2$CH$_2$, (NH$_2$)$_2$CH, CH$_3$O, CH$_3$CH$_2$O, CH$_3$OCH$_2$, CH$_3$NH or (CH$_3$)$_2$N.

In some embodiments of the present invention, $R_1$ is H.

In some embodiments of the present invention, $R_1$ is F.

In some embodiments of the present invention, $R_2$ is H.

In some embodiments of the present invention, $R_2$ is CH$_3$.

In some embodiments of the present invention, the configuration of the carbon atom bonded to $R_2$ is R.

In some embodiments of the present invention, the configuration of the carbon atom bonded to $R_2$ is S.

In some embodiments of the present invention, $R_3$ is selected from CN, halogen, C(=O)NH$_2$, or is selected from the group consisting of $C_{1-3}$ alkyl and $C_{1-3}$ heteroalkyl, each of which is optionally substituted by 1, 2 or 3 $R_0$.

In some embodiments of the present invention, $R_3$ is selected from CN, F, Cl, Br, CH$_3$, CH$_3$CH$_2$, CF$_3$, CHF$_2$, CH$_2$F, CH$_3$O or C(=O)NH$_2$.

In some embodiments of the present invention, A is selected from the group consisting of

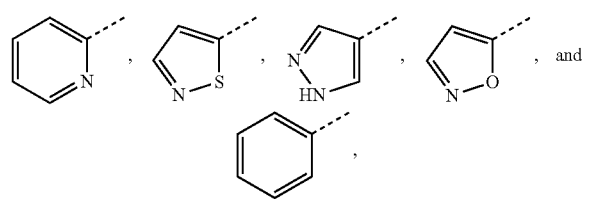

each of which is optionally substituted by 1, 2 or 3 $R_3$.

In some embodiments of the present invention, A is selected from the group consisting of

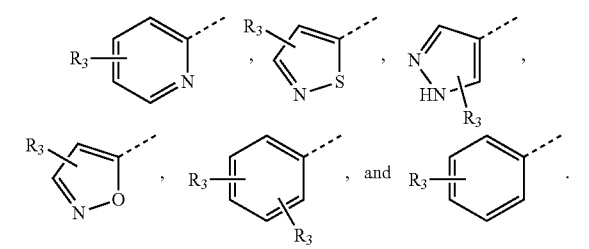

In some embodiments of the present invention, A is selected from the group consisting of

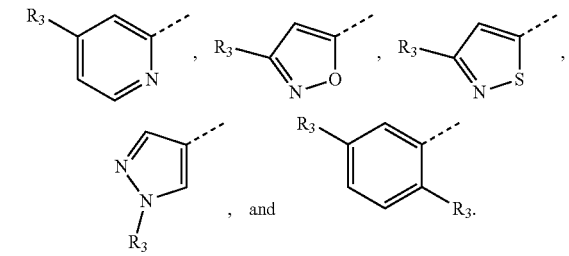

In some embodiments of the present invention, A is selected from the group consisting of

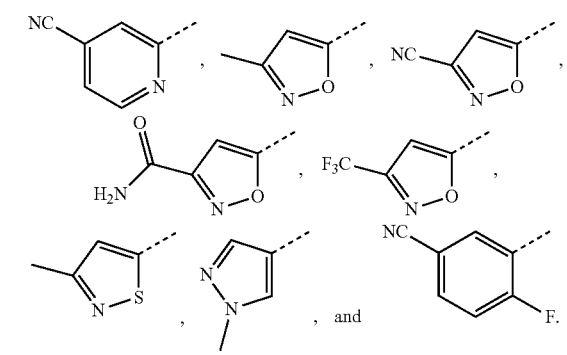

In some embodiments of the present invention, the compound above is selected from the group consisting of embodiment 1

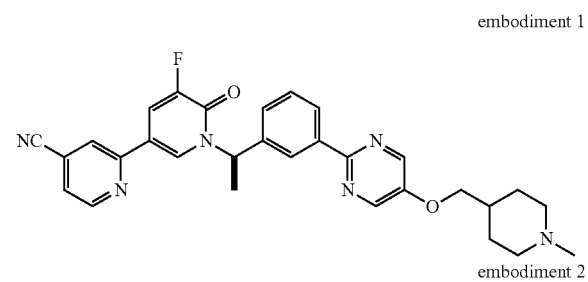

embodiment 2

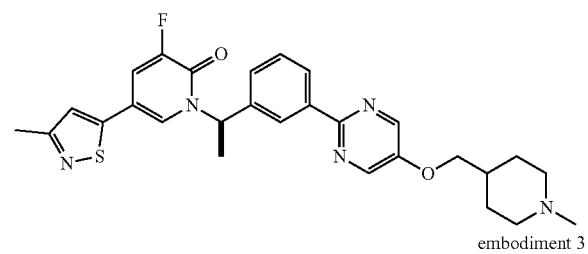

embodiment 3

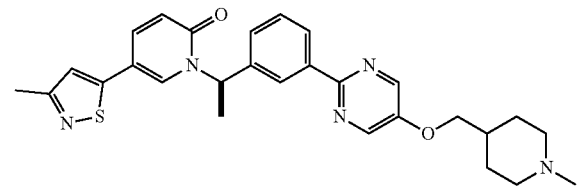

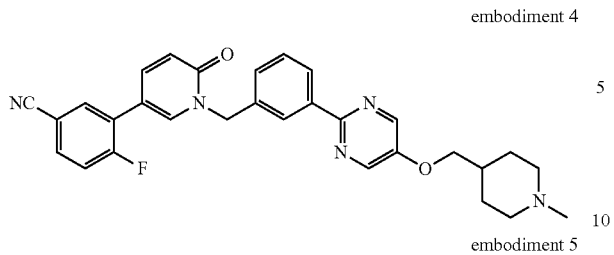

embodiment 4 embodiment 5 embodiment 6 embodiment 7 embodiment 8 embodiment 9 embodiment 10

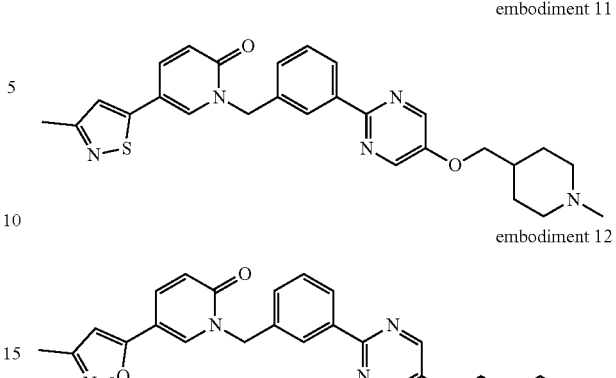

embodiment 11 embodiment 12

The present invention also provides a pharmaceutical composition comprising a therapeutically effective amount of the compound described above or the pharmaceutically acceptable salt thereof, as well as a pharmaceutically acceptable carrier.

The present invention also provides a use of the compound or the pharmaceutically acceptable salt thereof or the pharmaceutical composition described above in manufacturing a medicament for treating tumor.

Technical Effect

The present invention focused on the precise structural modification of the metabolic site, so that the metabolic stability of the targeted compound had been greatly improved. Besides, a brand new pyridone core structure was designed and synthesized to make the binding force between the targeted compounds and the C-Met enzyme significantly enhanced, thus obtained a more excellent activity for inhibiting tumor from growing. In the meanwhile, in vivo pharmacodynamics results showed that tumor growth rate of the mice who had been administered the compound of the present invention was significantly lower than that of Tepotinib EMD 1214063) at the same dose, further demonstrating that the compound of the present invention has better tumor inhibition activity. The compound of the present invention has a longer half-life time, an extended action time on the target, a more stable metabolic stability and a more excellent inhibitory activity.

Definition and Description

Unless otherwise indicated, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present invention contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including a hydrated form. Generally, the solvated form is equivalent to the unsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, a wedged bond and a dashed bond ( ) are used to indicate the absolute configuration of a stereogenic center,  and  are used to indicate the relative configuration of a stereogenic center. When the compound described herein contains an olefinic double bond or other geometric asymmetric centers, E and Z geometric isomers are included unless otherwise specified. Likewise, all tautomeric forms are encompassed within the scope of the present invention.

The compound of the present invention may present in a specific geometric or stereoisomeric form. The present invention contemplates all such compounds, including cis and trans isomer, (−)- and (+)-enantiomer (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present invention may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmac*, 21*st Ed, Lippincott, Williams & Wilkins* (2005), the disclosure of which is incorporated herein by reference.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient". "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When a bond of a substituent can be cross-linked to two atoms on a ring, such substituent can be bonded to any atom on the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the structural unit

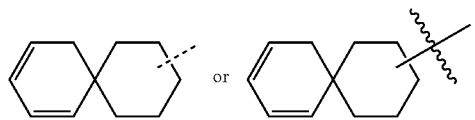

means that it can be substituted at any position on cyclohexyl or cyclohexadiene.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH2-CH2-O—CH3, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$. —S(O)—CH$_3$, —CH$_2$—CH$_2$—S(O)2-CH$_3$, —CH=CH—O—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "alkyl" refers to a linear chain or branched saturated hydrocarbon group, can be mono-substituted (e.g. —CH2F) or poly-substituted (e.g. —CF3), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo(C1-C4)alkyl" is meant to include, but not limited to, trifluoromethyl, 2,2,2-trifluoroethyl, 4-chlorobutyl, 3-bromopropyl and the like. Examples of haloalkyl include, but not limited to trifluommethyl, trichloromethyl, pentafluoroethyl and pentachloroethyl.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. The present invention employs the following abbreviations: aq represents water, HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; rt represents room temperature; O/N represents overnight; THF represents tetrahydrofuran; Boc$_2$O represents di-tert-butyldicarbonate; TFA represents trifluoroacetic acid: DIPEA represents diisopropylethylamine; SOCl$_2$ represents thionyl chloride; CS$_2$ represents carbon disulfide; TsOH represents p-toluenesulfonic acid; NFSI represents N-fluoro-N-(benzenesulfonyl) benzenesulfonamide; NCS represents N-chlorosuccinimide; n-Bu4NF represents tetrabutylammonium fluoride; iPrOH represents 2-propanol; mp represents melting point; LDA represents lithium diisopropylamide.

Compounds are named manually or by ChemDraw® software, the commercially available compounds use their vendor directory names.

DETAILED DESCRIPTION OF THE PREFERRED EMBODIMENT

The following embodiments further illustrate the present invention, but by all means the invention is not limited thereto. While the present invention has been described in detail and with reference to specific embodiments thereof, it will be apparent to those skilled in the art that various changes and modifications can be made therein without departing from the spirit and scope thereof.

Embodiment 1 (1-1 and 1-2)

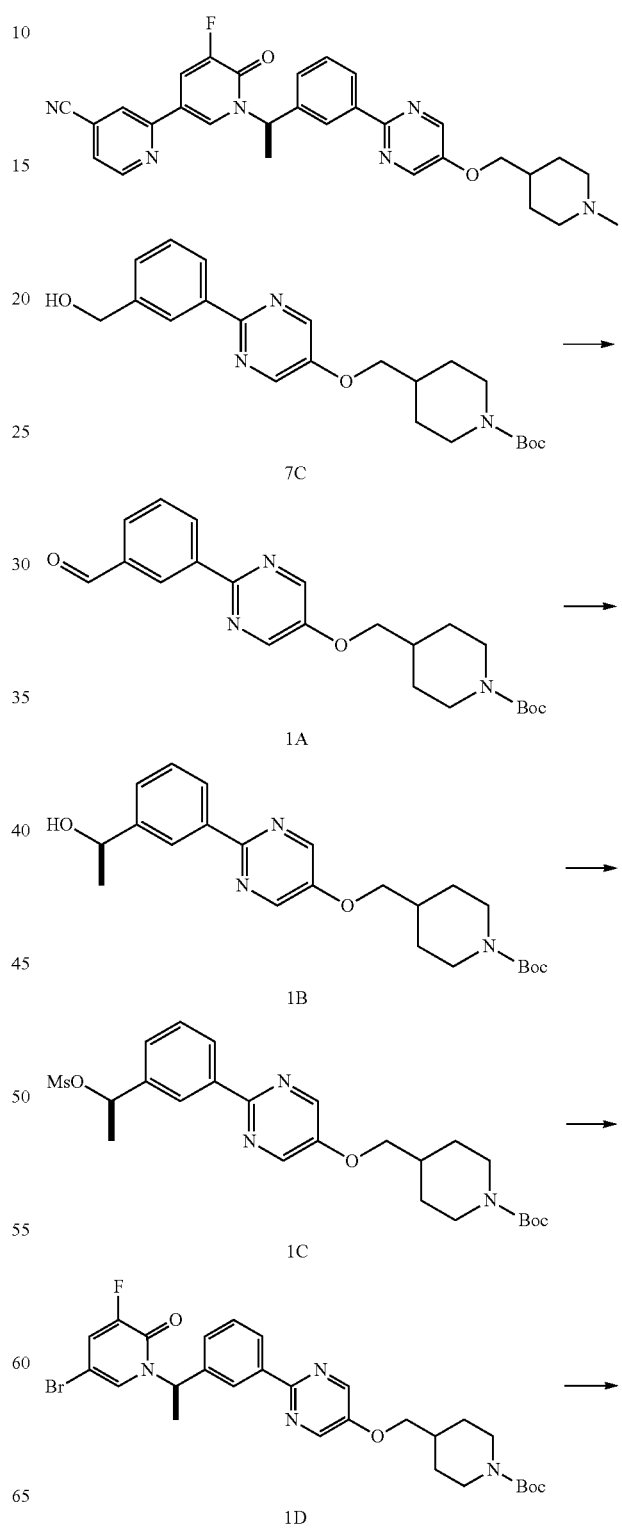

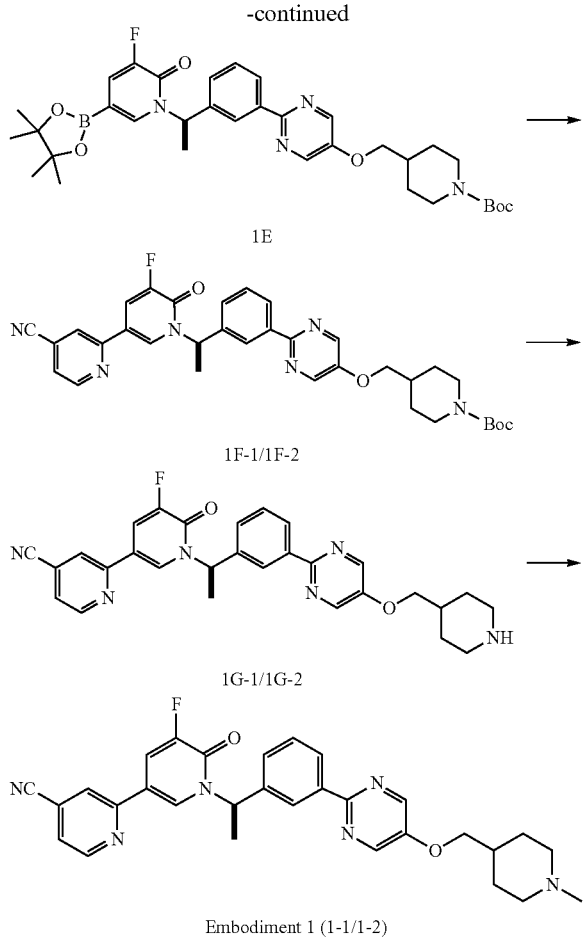

Embodiment 1 (1-1/1-2)

Step A:

The solution of intermediate 7C (synthetic method see embodiment 7) (20.4 g, 50.88 mmol) and manganese dioxide (44.23 g, 508.7 mmol) in DCM (300 mL) was stirred at room temperature for 16 hours. After the reaction was complete, the mixture was filtered and concentrated to give the intermediate 1A (18.4 g) which was used directly for the next step. LCMS (ESI) m/z: 398(M+1).

Step B:

Methylmagnesium bromide (3 M, 38.58 mL) was added into a solution of intermediate 1A (23.0 g, 57.87 mmol) in THF (200 mL) at 0° C. The solution was stirred at room temperature for 1 hour. After the reaction was complete, the mixture was quenched by saturated sodium chloride solution (300 mL), extracted by ethyl acetate (200 mL*2), dried over anhydrous sodium sulfate, filtered and concentrated to give intermediate 1B (22.76 g, yield 95.11%). LCMS (ESI) m/z: 414 (M+1). HNMR (400 MHz, CHLOROFORM-d) δ=8.46 (s, H), 8.38-8.33 (m, 1H), 8.26 (td, J=1.9, 6.9 Hz, 1H), 7.53-7.44 (m, 2H), 5.02 (q, J=6.4 Hz, 1H), 4.31-4.12 (m, 2H), 3.95 (d, J=6.4 Hz, 2H), 2.78 (hr t, J=12.1 Hz, 2H), 2.13 (br s, 1H), 2.08-1.96 (m, 1H), 1.86 (br d, J=12.9 Hz, 2H), 1.58 (d, J=6.5 Hz, 3H), 1.49 (s, 9H), 1.39-1.29 (m, 2H).

Step C:

Diisopropylethylamine (21.34 g, 165.12 mmol) and methanesulfonyl chloride (9.12 g, 79.62 mmol) were added into a solution of intermediate 1B (22.7 g, 55.04 mmol) in DCM (300 mL) at 0° C. The reaction solution was stirred at room temperature for 1 h. After the reaction was complete as monitored by TLC, the mixture was washed with saturated ammonium chloride solution (200 mL) twice, dried over anhydrous sodium sulfate, filtered and concentrated to give the intermediate 1C (30 g, crude product) which was used directly for the next step.

Step D:

Potassium carbonate (10.68 g, 77.30 mmol), potassium iodide (641.58 mg, 3.86 mmol) and 5-bromo-3-fluoro-1H-pyridin-2-one (11.13 g, 57.97 mmol) were added into a solution of intermediate 1C (19 g, 3.86 mmol) in DMF (100 mL) at room temperature. The reaction solution was stirred at 90° C. for 3 hours. After the reaction was complete, ethyl acetate (300 mL) was added into the solution and the solution was washed with brine (300 mL) three times. The organic phase was dried over anhydrous sodium sulfate, filtered and concentrated to give the intermediate 1D (5.8 g, yield 25.54%). HNMR (400 MHz, CHLOROFORM-d) S=8.47 (s, 2H), 8.41-8.32 (m, 2H), 7.55-7.47 (m, 1H), 7.39 (d, J=7.7 Hz, 1H), 7.15 (dd, J=2.4, 8.4 Hz, 1H), 7.11-7.07 (m, 1H), 6.52 (q, J=7.0 Hz, 1H), 4.31-4.12 (m, 2H), 4.01-3.93 (m, 2H), 2.87-2.72 (m, 2H), 2.09-1.98 (m, 1H), 1.89-1.80 (m, 5H), 1.49 (s, 9H), 1.39-1.30 (m, 2H).

Step E:

Under nitrogen atmosphere, intermediate 1D (2.0 g, 3.4 mmol), 4,4,5,5-tetramethyl-2-(4,4,5,5-tetramethyl-1,3,2-dioxaborolan-2-yl)-1,3,2-dioxaborolane (1.04 g, 4.09 mmol), acetate potassium (668.21 mg, 6.81 mmol) and Pd(dppf)Cl$_2$ (498.20 mg, 680.87 μmol) were dissolved in dioxane (30 mL) at room temperature. The reaction solution was stirred at 90° C. for 2 hours. After the reaction was complete, a solution (30 mL) of intermediate 1E in dioxane was obtained and used directly for the next step.

Step F (1F-1, 1F-2):

Under nitrogen atmosphere, a solution (30 mL) of intermediate 1E (1.92 g, 3.03 mmol) in dioxane, sodium carbonate (642.30 mg, 6.06 mmol), 2-bromo-5-cyanopyridine (665.42 mg, 3.64 mmol) and Pd(dppf)Cl$_2$ (443.43 mg, 606.0 μmol) were dissolved in dioxane (40 mL) and water (6 mL) at room temperature. The reaction was stirred at 90° C. for 3 hours. After the reaction was complete, the mixture was filtered and water (100 mL) was added into the filtrate and extracted with ethyl acetate (60 mL*3). The organic phase was dried over anhydrous sodium sulfate and then filtered and concentrated. The crude product was purified by preparative plate, and the intermediate 1F-1 (t=2.819, 490 mg, 26.04% yield) and intermediate 1F-2 (t=3.933, 480 mg, 25.95% yield) were isolated by SFC (column type: AS (250 mm*30 mm, 10 um); mobile phase: [B: 0.1% NH$_3$H$_2$O EtOH]; B° %: 55%-55%, 10 min; 200 minmin).

LCMS (ESI) m/z: 611 (M+1).

HNMR (intermediate 1F-1) (400 MHz, METHANOL-d4) δ=8.73 (dd, J=0.9, 5.0 Hz, 1H), 8.55 (s, 2H), 8.39 (s, 1H), 8.34-8.26 (m, 2H), 8.17-8.08 (m, 2H), 7.58-7.49 (m, 3H), 6.50 (q, J=7.2 Hz, 1H), 4.15 (br d, J=13.3 Hz, 2H), 4.06 (d, J=6.3 Hz, 2H), 2.84 (br s, 2H), 2.14-2.01 (m, 1H), 1.97 (d, J=7.3 Hz, 3H), 1.87 (br d, J=11.9 Hz, 2H), 1.48 (s, 9H), 1.35-1.28 (m, 2H).

HNMR (intermediate 1F-2) (400 MHz, METHANOL-d4) δ=8.73 (dd, J=0.8, 5.0 Hz, 1H), 8.55 (s, 2H), 8.39 (s, 1H), 8.34-8.26 (m, 2H), 8.16-8.09 (m, 2H), 7.61-7.49 (m, 3H), 6.50 (q, J=7.2 Hz, 1H), 4.15 (br d, J=13.2 Hz, 2H), 4.06 (d, J=6.3 Hz, 2H), 2.84 (br s, 2H), 2.12-2.01 (m, 1H), 1.99-1.95 (m, 3H), 1.87 (br d, J=10.9 Hz, 2H), 1.48 (s, 9H), 1.35-1.29 (m, 2H).

Step G (1G-1, 1G-2)

Trifluoroacetic acid (3 mL) was added into a solution of intermediate 1F-1 (490 mg, 786.01 μmol) in DCM (10 mL)

at 0° C. The reaction solution was stirred at room temperature for 1 hour. After the reaction was complete, the mixture was evaporated to dryness to give intermediate 1G-1 (502 mg, crude product) which was directly used for the next step. Intermediate 1G-2 (491 mg, crude product) was obtained with the same method as intermediate 1G-1.

Step H:

Formalin (326.27 mg, 4.02 mmol, 37% purity) and sodium triacetoxyborohydride (511.03 mg, 2.41 mmol) were added into a solution of intermediate 1G-1 (502.00 mg, 803.74 mmol) in DCM (10 mL) at 0° C. The reaction solution was stirred at room temperature for 2 hours. After the reaction was complete, the mixture was quenched with water (50 mL) and DCM (30 mL*2). The organic phase was dried over anhydrous sodium sulfate, filtered and concentrated. The crude product obtained was purified by preparative HPLC to give the embodiment 1-1 (150 mg, 35.41% yield).

Embodiment 1-2 (100.6 mg, 23.91% yield) was obtained with the same method as embodiment 1-1, started from intermediate 1G-2.

Embodiment 1-1

LCMS (ESI) m/z: 525 (M+1).

HNMR (400 MHz, METHANOL-d4) δ=8.73 (d, J=4.9 Hz, 1H), 8.56 (s, 2H), 8.49 (s, 1H), 8.39 (s, 1H), 8.34-8.26 (m, 2H), 8.18-8.09 (m, 2H), 7.61-7.49 (m, 3H), 6.50 (q, J=7.2 Hz, 1H), 4.13 (d, J=5.8 Hz, 2H), 3.53 (br d, J=12.4 Hz, 2H), 3.03 (br t, J=12.4 Hz, 2H), 2.87 (s, 3H), 2.27-2.08 (m, 3H), 1.97 (d, J=7.2 Hz, 3H), 1.81-1.63 (m, 2H).

Embodiment 1-2

LCMS (ESI) m/z: 525 (M+1).

HNMR (400 MHz, METHANOL-d4) δ=8.72 (dd, J=0.8, 5.0 Hz, 1H), 8.61-8.46 (m, 3H), 8.38 (s, 1H), 8.33-8.25 (m, 2H), 8.16-8.08 (m, 2H), 7.58-7.47 (m, 3H), 6.49 (q, J=7.1 Hz, 1H), 4.12 (d, J=5.9 Hz, 2H), 3.50 (br d, J=12.2 Hz, 2H), 3.05-2.93 (m, 2H), 2.83 (s, 3H), 2.22-2.06 (m, 3H), 1.96 (d, J=7.2 Hz, 3H), 1.80-1.62 (m, 2H).

Embodiment 2 (2-1 and 2-2)

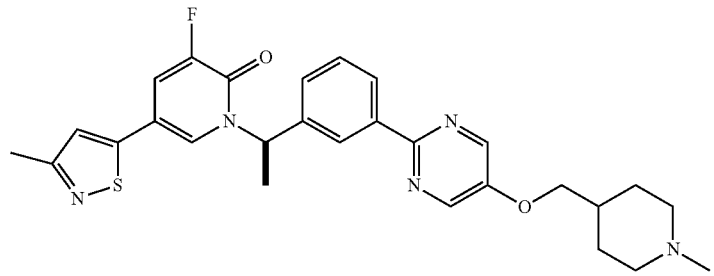

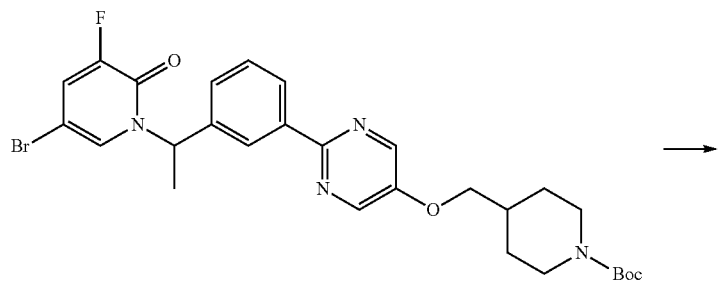

1D

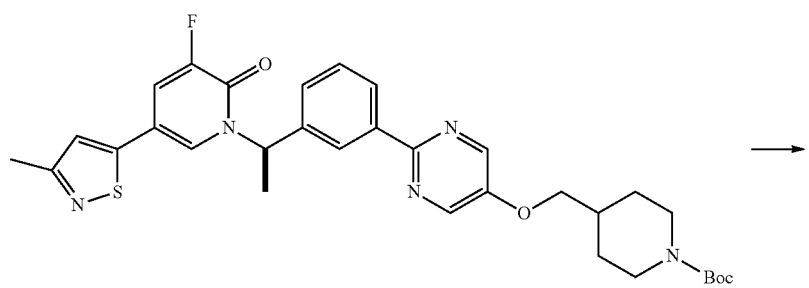

2A-1/2A-2

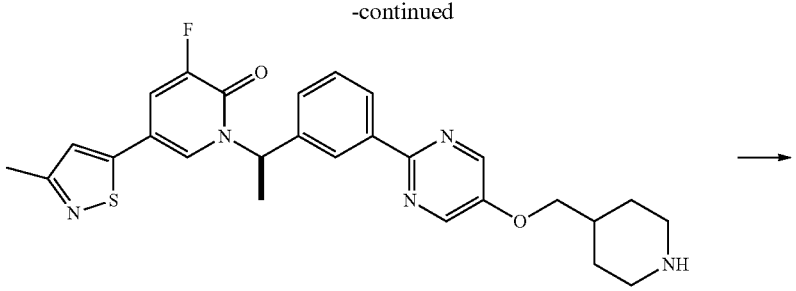

2B-1/2B-2

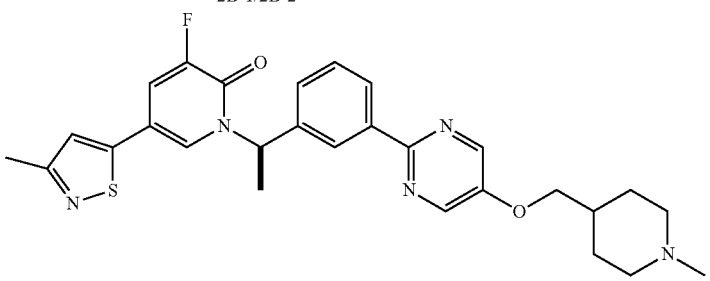

Embodiment (2-1/2-2)

Step A:

Under nitrogen atmosphere, intermediate 1D (1.0 g*2, 1.70 mmol), 3-methyl-5-(4,4,5,5-tetramethyl-1,3,2-dioxaborolane-2-yl)isothiazole (1.15 g, 5.10 mmol), potassium phosphate (1 M, 3.4 mL) and 1,1-(tert-butylphosphino)ferrocene palladium dichloride (110.80 mg, 170.00 μmol) were dissolved in THF (10 mL) at room temperature. The reaction solution was stirred at 70° C. for 16 hours. The reaction solution was then filtered and water (50 mL) was added into. The mixture was extracted by ethyl acetate (30 mL*3). The organic phase was then dried over anhydrous sodium sulfate, filtered and concentrated. The crude product was then purified by preparative HPLC. The intermediate 2A-1 (t=2.529, 560 mg, 24.28% yield) and intermediate 2A-2 (t=3.494, 500 mg, 27.19% yield) were isolated by SFC (column type: AS (250 mm*30 mm, 10 um); mobile phase: [B: 0.1% NH$_3$H$_2$O EtOH]: B %: 35%-35%, 7.2 min; 200 minmin).

LCMS (ESI) m/z: 605 (M+1)

HNMR (intermediate 2A-1) (400 MHz, METHANOL-d4) δ=8.61-8.50 (m, 2H), 8.41-8.26 (m, 2H), 7.76 (d, J=2.1 Hz, 1H), 7.70 (dd, J=2.1, 10.0 Hz, 1H), 7.57-7.50 (m, 2H), 7.29 (s, 1H), 6.45 (q, J=7.1 Hz, 1H), 4.16 (br d, J=13.3 Hz, 2H), 4.07 (d, J=6.1 Hz, 2H), 2.85 (br s, 2H), 2.45 (s, 3H), 2.08 (br s, 1H), 1.96-1.84 (m, 5H), 1.48 (s, 9H), 1.37-1.29 (m, 2H).

HNMR (intermediate 2A-2) (400 MHz, METHANOL-d4) δ=8.59-8.53 (m, 2H), 8.41-8.27 (m, 2H), 7.76 (s, 1H), 7.73-7.66 (m, 1H), 7.58-7.49 (m, 2H), 7.28 (d, J=2.8 Hz, 1H), 6.45 (q, J=6.9 Hz, 1H), 4.16 (br d, J=13.6 Hz, 2H), 4.06 (dd, J=3.9, 6.1 Hz, 2H), 2.94-2.78 (m, 2H), 2.44 (d, J=2.1 Hz, 3H), 2.07 (td, J=3.7, 9.6 Hz, 1H), 1.96-1.84 (m, 5H), 1.48 (s, 9H), 1.36-1.27 (m, 2H).

Step B: intermediate 2B-1 and intermediate 2B-2 were prepared according to the preparation method of intermediate 1G-1.

Step C: embodiment 2-1 and 2-2 were prepared according to the preparation method of embodiment 1.

Embodiment 2-1

LCMS (ESI) m/z: 520 (M+1).

HNMR (400 MHz, METHANOL-d4) δ=8.73 (s, 2H), 8.35 (s, 1H), 8.29 (d, J=7.2 Hz, 1H), 7.86-7.81 (m, 1H), 7.72 (dd, J=2.3, 10.0 Hz, 1H), 7.64-7.58 (m, 2H), 7.36 (s, 1H), 6.45 (q, J=7.1 Hz, 1H), 4.21 (d, J=5.9 Hz, 2H), 3.63 (br d, J=12.4 Hz, 2H), 3.15 (br t, J=11.9 Hz, 2H), 2.92 (s, 3H), 2.47 (s, 3H), 2.33-2.06 (m, 3H), 1.99 (d, J=7.2 Hz, 3H), 1.86-1.73 (m, 2H).

Embodiment 2-2

LCMS (ESI) m/z: 520 (M+1).

HNMR (400 MHz, METHANOL-d4)=8.75 (s, 2H), 8.37 (s, 1H), 8.28 (d, J=7.2 Hz, 1H), 7.88-7.81 (m, 1H), 7.70 (dd, J=2.3, 10.0 Hz, 1H), 7.65-7.56 (m, 2H), 7.34 (s, 1H), 6.42 (q, J=7.1 Hz, 1H), 4.20 (d, J=5.9 Hz, 2H), 3.62 (br d, J=12.4 Hz, 2H), 3.12 (br t, J=11.9 Hz, 2H), 2.91 (s, 3H), 2.45 (s, 3H), 2.33-2.08 (m, 3H), 1.96 (d, J=7.2 Hz, 3H), 1.87-1.70 (m, 2H).

Embodiment 3

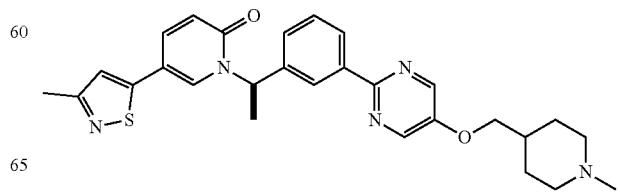

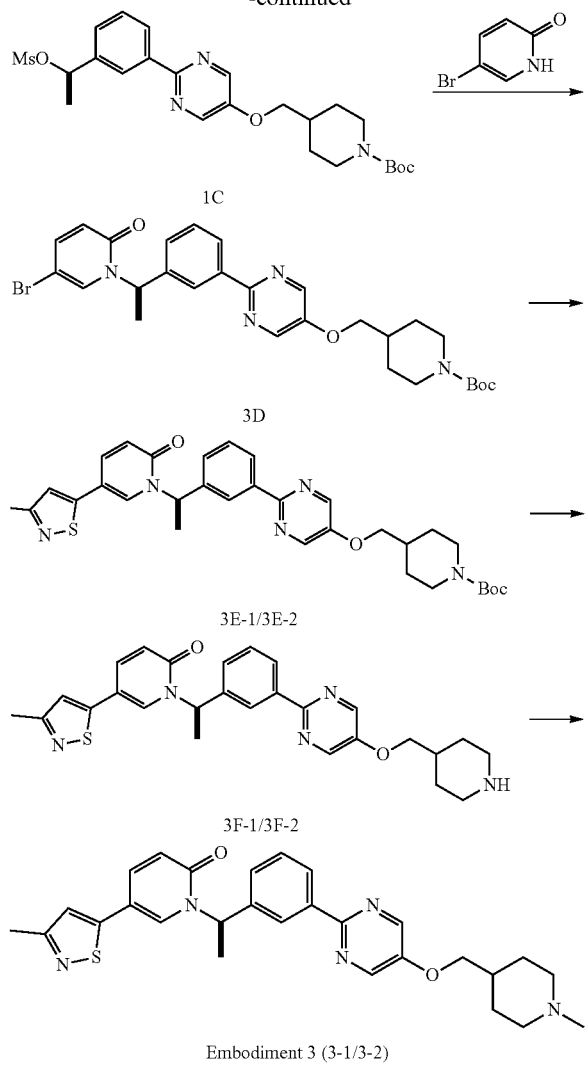

3D 3E-1/3E-2

3F-1/3F-2

Embodiment 3 (3-1/3-2)

Step A:
Intermediate 3D was prepared according to the preparation method of intermediate 1D.

Step B:
Intermediate 3E was prepared according to the preparation method of intermediate 1F. The intermediate 3E-1 (t=2.805, 33 mg, 33.0% yield) and intermediate 3E-2 (t=3.255, 33 mg, 33% yield) were isolated by SFC (column type: AS (250 mm*30 mm, 10 um); mobile phase: [B: 0.1% $NH_3H_2O$ EtOH]; B %: 40%-40%, 5 min; 80 minmin). LCMS (ESI) m/z: 588 (M+1).

Step C:
Intermediate 3F-1 (580 mg, crude product) and 3F-2 (520 mg, crude product) were prepared according to the preparation method of intermediate 1G.

Step D:
Embodiment 3-1 and 3-2 were prepared according to the preparation method of embodiment 1.

Embodiment 3-1

LCMS (ESI) m z: 502 (M+1).
HNMR (400 MHz, METHANOL-d4) δ=8.62-8.49 (m, 3H), 8.36 (s, 1H), 8.31 (br d, J=6.8 Hz, 1H), 7.91 (s, 1H), 7.77 (br d, J=9.4 Hz, 1H), 7.57-7.49 (m, 2H), 7.26 (s, 1H), 6.71 (d, J=9.4 Hz, 1H), 6.42 (q, J=6.6 Hz, 1H), 4.13 (br d, J=5.1 Hz, 2H), 3.50 (br d, J=11.9 Hz, 2H), 2.97 (br t, J=12.2 Hz, 2H), 2.83 (s, 3H), 2.44 (s, 3H), 2.24-2.06 (m, 3H), 1.91 (br d, J=7.1 Hz, 3H), 1.80-1.61 (m, 2H).

Embodiment 3-2

LCMS (ESI) m/z: 502 (M+1).
HNMR (400 MHz, METHANOL-d4) δ=8.56 (s, 2H), 8.49 (br s, 1H), 8.36 (s, 1H), 8.30 (br d, J=6.7 Hz, 1H), 7.91 (d, J=2.4 Hz, 1H), 7.77 (dd, J=2.4, 9.4 Hz, 1H), 7.56-7.49 (n, 2H), 7.26 (s, 1H), 6.70 (d, J=9.4 Hz, 1H), 6.41 (q, J=7.1 Hz, 1H), 4.13 (d, J=5.7 Hz, 2H), 3.54 (br d, J=12.3 Hz, 2H), 3.05 (br t, J=11.9 Hz, 2H), 2.87 (s, 3H), 2.44 (s, 3H), 2.21-2.08 (m, 3H), 1.91 (d, J=7.1 Hz, 3H), 1.79-1.67 (m, 2H).

Embodiment 4

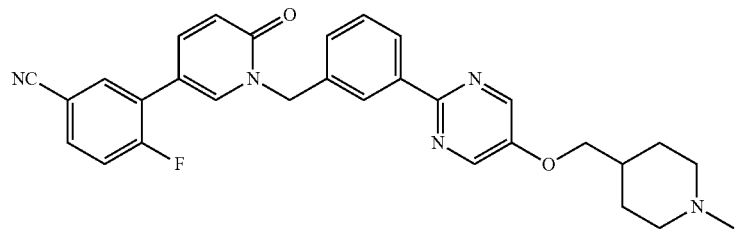

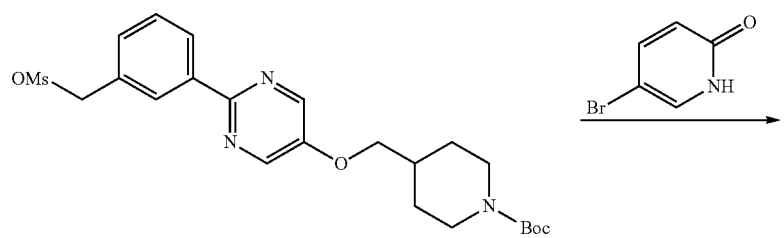

7D

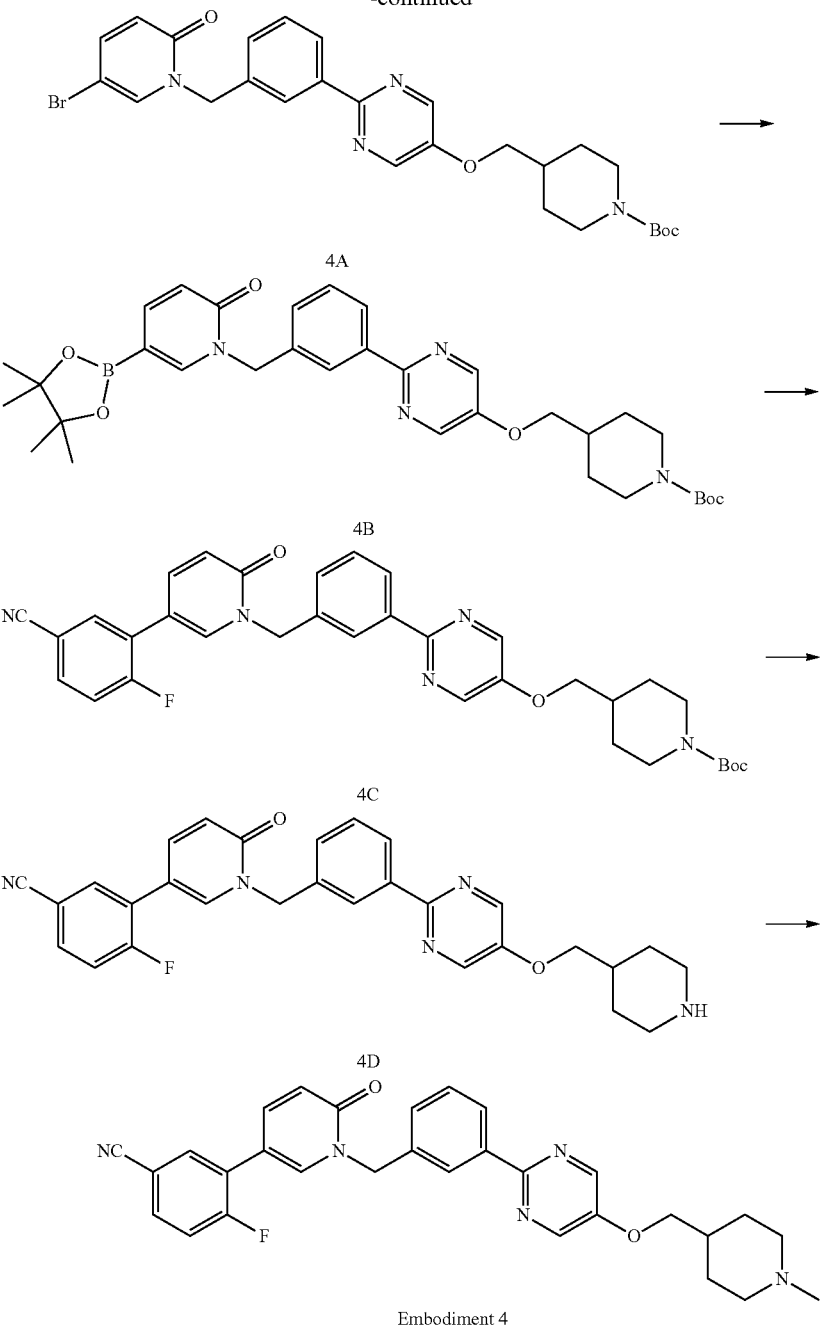

Step A:
Intermediate 4A was prepared according to the preparation method of intermediate 1D.
Step B:
Intermediate 4B was prepared according to the preparation method of intermediate 1E.
Step C:
Intermediate 4C was prepared according to the preparation method of intermediate 1F.
Step D:
Intermediate 4D was prepared according to the preparation method of intermediate 1G.

Step E:
Embodiment 4 was prepared according to the preparation method of embodiment 1. LCMS (ESI) m/z: 510 (M+1). HNMR (400 MHz, METHANOL-d4)=8.59-8.47 (m, 3H), 8.37 (s, 1H), 8.32-8.24 (m, 1H), 8.17 (d, J=2.5 Hz, 1H), 7.95 (dd, J=2.0, 7.3 Hz, 1H), 7.85-7.73 (m, 2H), 7.51-7.46 (m, 2H), 7.41 (dd, J=8.6, 10.5 Hz, 1H), 6.70 (d, J=9.5 Hz, 1H), 5.37 (s, 2H), 4.12 (d, J=5.8 Hz, 2H), 3.52 (br d, J=12.8 Hz, 2H), 3.08-2.96 (m, 2H), 2.85 (s, 3H), 2.26-2.09 (m, 3H), 1.79-1.63 (m, 2H).

Embodiment 5
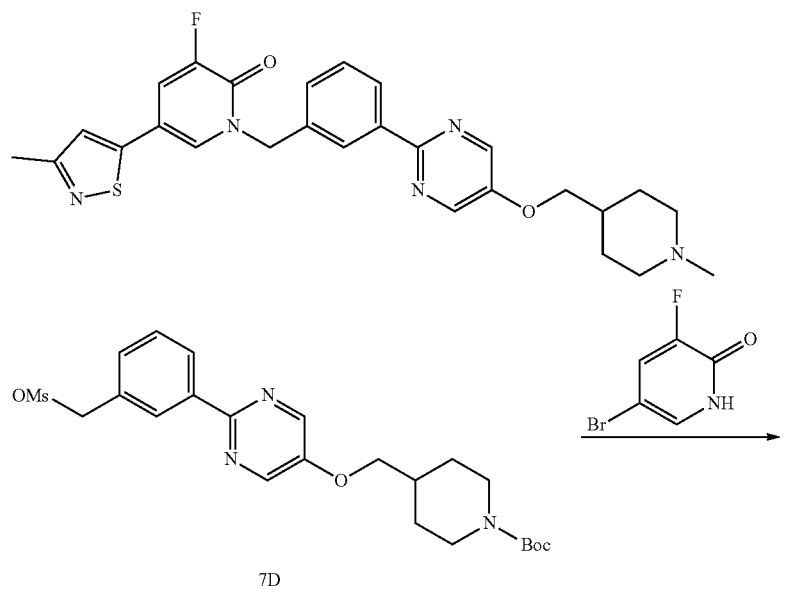
7D
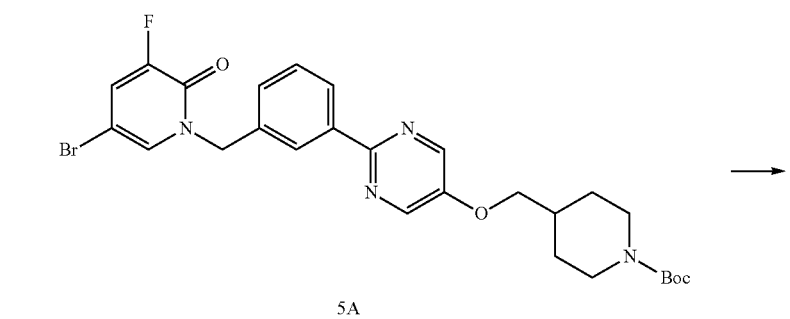
5A
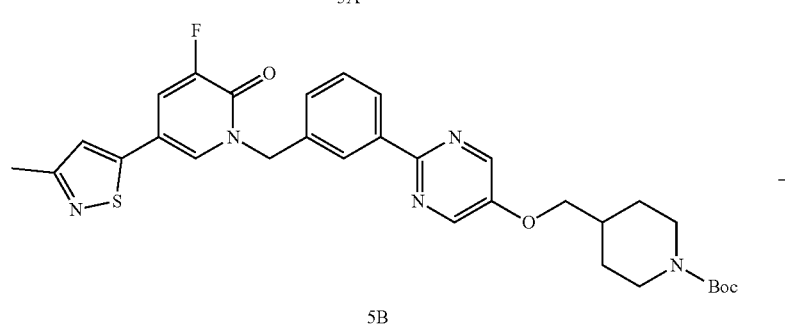
5B
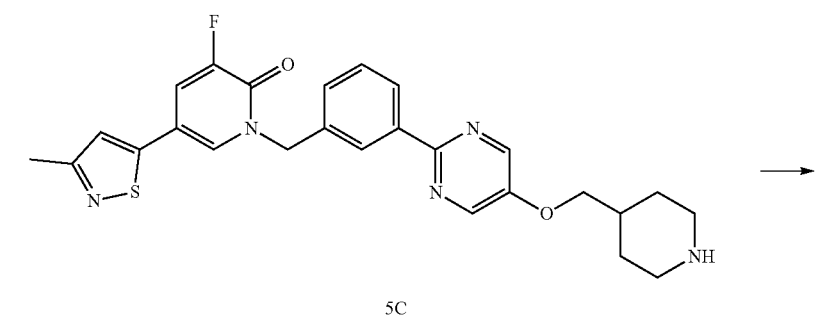
5C

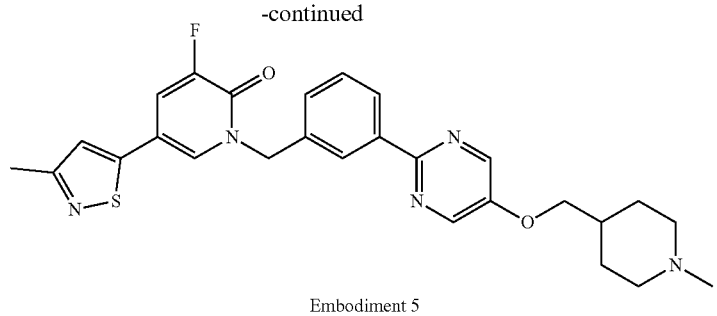

Embodiment 5

Step A:

Intermediate 5A was prepared according to the preparation method of intermediate 1D.

Step B:

Intermediate 5B was prepared according to the preparation method of intermediate 1F.

Step C:

Intermediate 5C was prepared according to the preparation method of intermediate 1G.

Step D:

Embodiment 5 was prepared according to the preparation method of Embodiment 1. LCMS (ESI) m/z: 506 (M+1). HNMR (400 MHz, METHANOL-d4)=8.58-8.49 (m, 3H), 8.37-8.26 (m, 2H), 8.16 (dd, J=1.3, 2.1 Hz, 1H), 7.74 (dd, J=2.2, 10.2 Hz, 1H), 7.50 (d, J=5.3 Hz, 2H), 7.34 (s, 1H), 5.40 (s, 2H), 4.12 (d, J=5.8 Hz, 2H), 3.51 (br d, J=12.4 Hz, 2H), 3.06-2.94 (m, 2H), 2.84 (s, 3H), 2.47 (s, 3H), 2.23-2.07 (m, 3H), 1.80-1.62 (m, 2H).

Embodiment 6

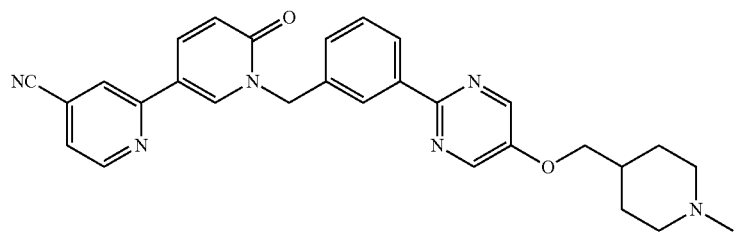

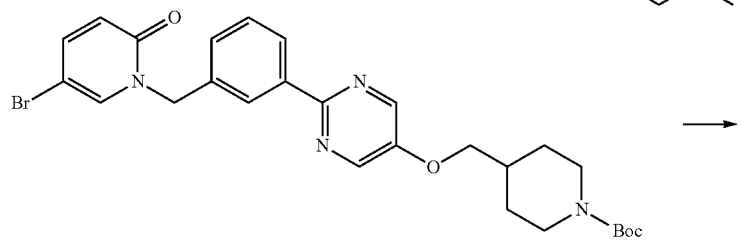

4A

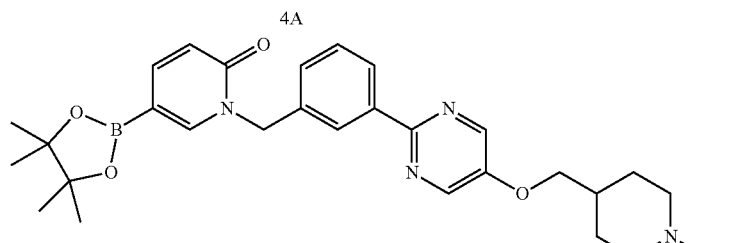

6A

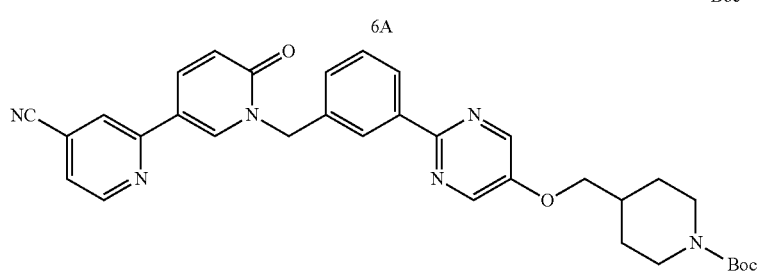

6B

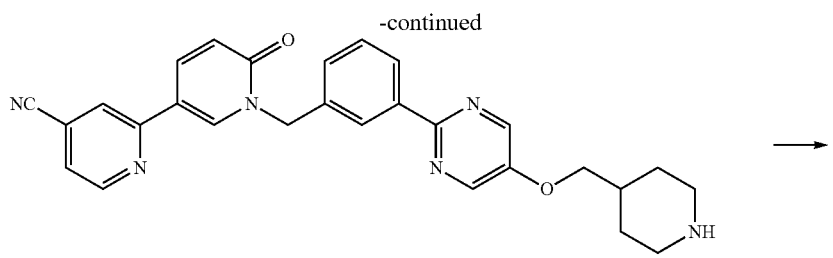

6C

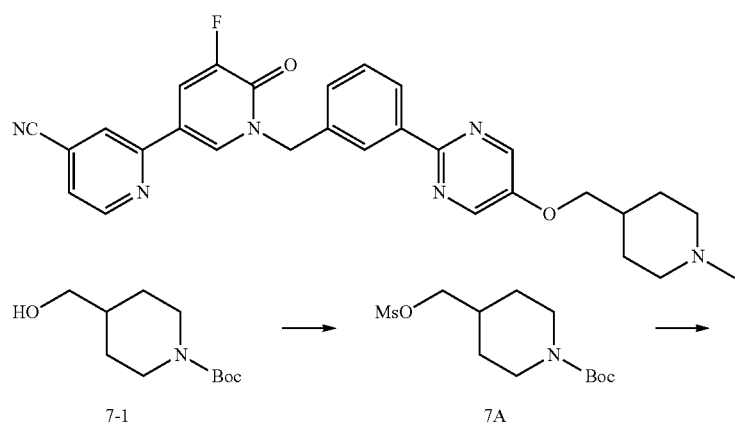

Embodiment 6

Step A:

Intermediate 6A was prepared according to the preparation method of intermediate 1E.

Step B:

Intermediate 6B was prepared according to the preparation method of intermediate 1F.

Step C:

Intermediate 6C was prepared according to the preparation method of intermediate 1G.

Step D:

Embodiment 6 was prepared according to the preparation method of Embodiment 1. LCMS (ESI) m/z: 493 (M+1). HNMR (400 MHz. METHANOL-d4) δ=8.75 (d, J=5.0 Hz, 1H), 8.69 (d, J=2.4 Hz, 1H), 8.58-8.43 (m, 3H), 8.34 (s, 1H), 8.30-8.22 (m, 2H), 8.13 (s, 1H), 7.55 (dd, J=1.1, 5.0 Hz, 1H), 7.51-7.44 (m, 2H), 6.71 (d, J=9.5 Hz, 1H), 5.39 (s, 2H), 4.10 (d, J=5.9 Hz, 2H), 3.54 (br d, J=12.0 Hz, 2H), 3.04 (br t, J=12.0 Hz, 2H), 2.87 (s, 3H), 2.23-2.07 (m, 3H), 1.79-1.65 (m, 2H).

Embodiment 7

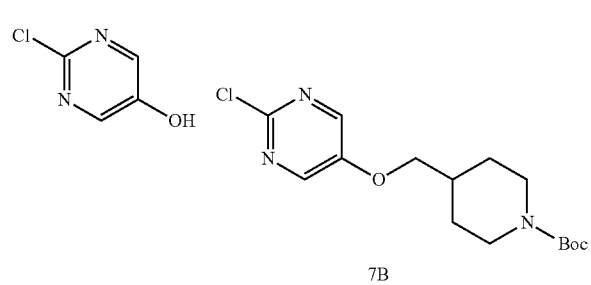

-continued
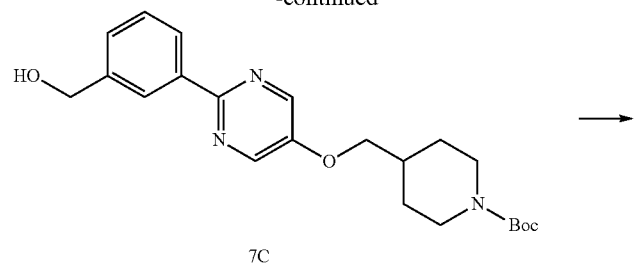
7C
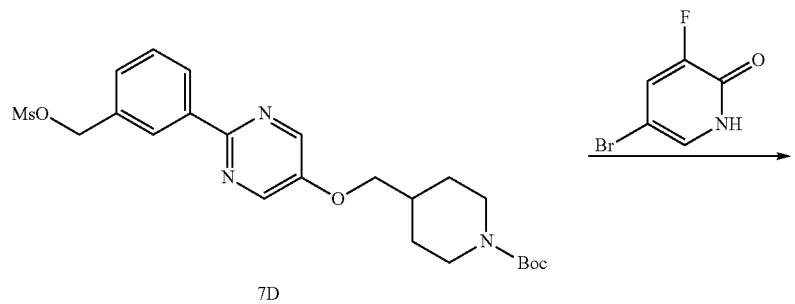
7D
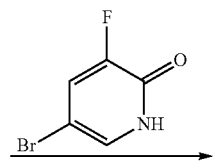
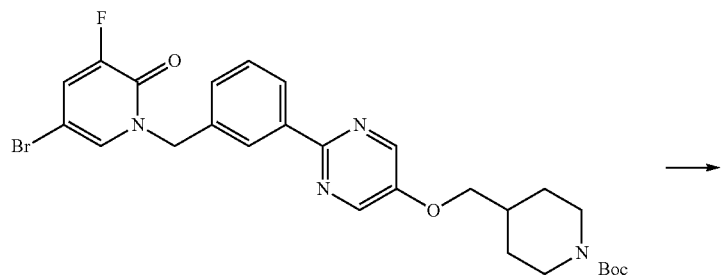
7E
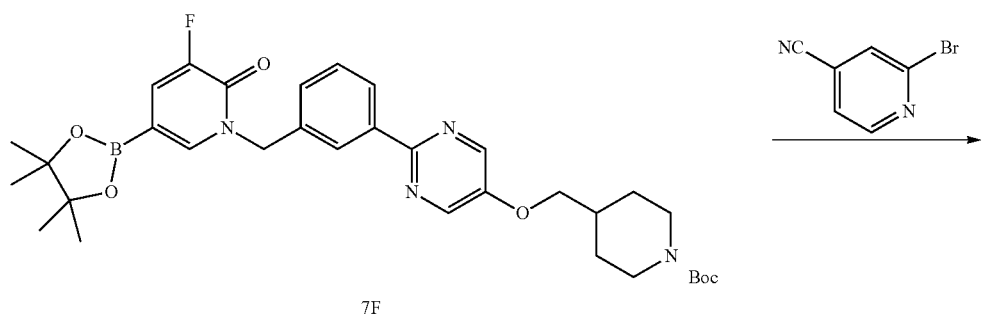
7F
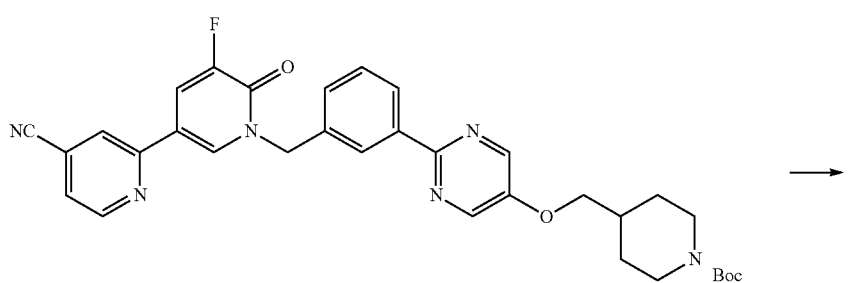
7G

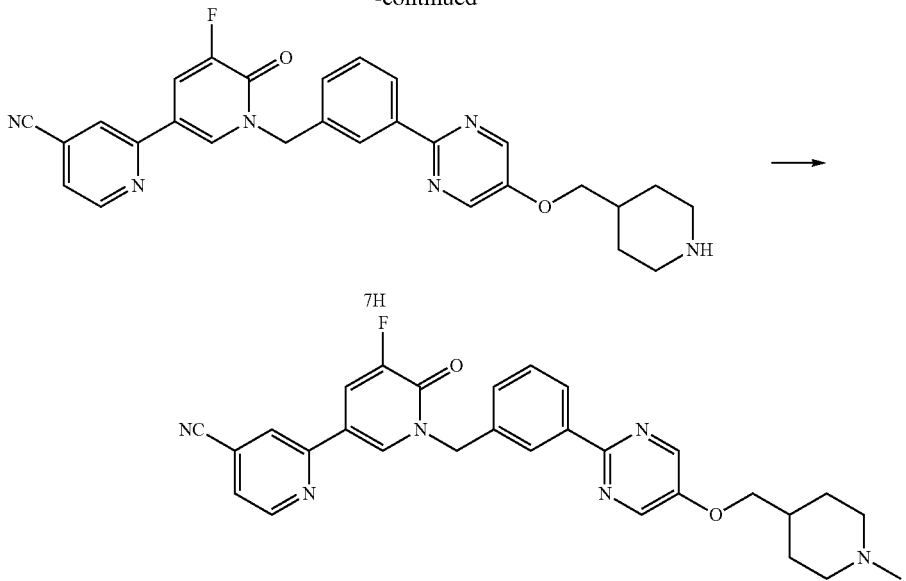

Embodiment 7

Step A:

Under nitrogen atmosphere, methane disulfonyl chloride (45.15 g, 394.15 mmol) was added dropwise into a solution of tert-butyl-4-(hydroxymethyl)piperidine-1-carbomate (68.00 g, 315.85 mmol) and diisopropylethylamine (81.64 g, 631.71 mmol) in dichloromethane (800 mL) while stirring. After the dropwise addition was complete, the reaction solution was stirred at 25° C. for 2 hours. Thin layer chromatography was used to ensure the reaction was complete. The reaction solution was washed with saturated ammonium chloride solution (500 mL*2) and brine (300 mL*2) and dried over anhydrous sodium sulfate, filtered and concentrated to give intermediate 7A (red oily liquid, 95.00 g, 100% yield) which was used directly for the next step without further purification.

Step B

Under nitrogen atmosphere, potassium carbonate (74.12 g, 536.28 mmol) was added into a solution of intermediate 7A (94.40 g, 321.77 mmol) and 2-chloropyrimidin-5-ol (35.00 g, 268.14 mmol) in DMF (1.00 L). The reaction solution was left at 80° C. for 16 hours, and thin layer chromatography was used to detect the completion of the reaction. Then the reaction solution was cooled to room temperature and concentrated, then water (500 mL) was added into the residue and extracted with ethyl acetate (300 mL*3). The organic phase was washed with brine (400 mL*2) and dried over anhydrous sodium sulfate, then filtered and concentrated. Then the residue was purified by column chromatography to give the intermediate 7B (pale yellow solid, 84.00 g, 95.05% yield). LCMS (ESI) m/z: 327.7 (M+1). 1HNMR (400 MHz, DMSO-d6) δ ppm 1.08-1.25 (m, 2H) 1.40 (s, 9H) 1.69-1.78 (m, 2H) 1.88-2.03 (m, 1H) 2.58-2.88 (m, 2H) 3.89-4.05 (m, 4H) 8.50-8.57 (m, 2H)

Step C:

Under nitrogen atmosphere, a mixed solution of intermediate 7B (84.00 g, 254.85 mmol), [3-(hydroxymethyl)phenyl]boronic acid (42.60 g, 280.34 mmol), Pd(PPh$_3$)$_2$Cl$_2$ (17.89 g, 25.49 mmol) and potassium carbonate (70.45 g, 509.71 mmol) in 1,4-dioxane (1.00 L) and water (200.00 mL) was stirred at 80° C. for 16 hours. Then the reaction solution was cooled to room temperature then filtered, followed by extraction with dichloromethane (500 mL*3), then the organic layers were combined together, washed with brine (500 mL*2) and dried over anhydrous sodium sulfate, then filtered and concentrated. The residue was recrystallized with methanol to give intermediate 7C (white solid, 77.60 g, 76.22% yield). LCMS (ESI) m/z: 400.1 (M+1). 1HNMR (400 MHz, DMSO-d6) δ ppm 1.14-1.31 (m, 2H) 1.45 (s, 9H) 1.75-1.87 (m, 2H) 1.95-2.10 (m, 1H) 2.66-2.93 (m, 2H) 3.94-4.22 (m, 4H) 4.63 (d, J=5.62 Hz, 2H) 5.34 (t, J=5.81 Hz, 1H) 7.41-7.54 (m, 2H) 8.21 (d, J=7.46 Hz, 1H) 8.35 (s, 1H) 8.68 (s, 2H)

Step D:

Under nitrogen atmosphere, methane disulfonyl chloride (3.44 g, 30.04 mmol) was added dropwise into a solution of intermediate 7C (10.00 g, 25.03 mmol) and diisopropylethylamine (6.47 g, 50.06 mmol) in dichloromethane (100.00 mL) while stirring. After the addition was complete, the reaction solution was stirred at 25° C. for 2 hours. The thin layer chromatography was used to detect the completion of the reaction. The reaction solution was washed with saturated ammonium chloride solution (500 mL*2) and brine (300 mL*2), dried over anhydrous sodium chloride, filtered and concentrated to give intermediate 7D (gray solid, 14.00 g, 100% yield) which was used directly for the next step without further purification. LCMS (ESI) m/z: 478.1 (M+).

Step E:

Under nitrogen atmosphere, potassium carbonate (6.95 g, 50.26 mmol) was added into a solution of intermediate 7D (12.00 g, 25.13 mmol) and 5-bromo-3-fluoro-1-H-pyridin-2-one (5.79 g, 30.16 mmol) in DMF (100.00 mL) at 25° C. The reaction solution was left at 90° C. for 3 hours, then the reaction was complete as monitored by thin layer chromatography. Then the reaction solution was cooled to room temperature and concentrated. The residue was washed by water (100 mL), extracted with ethyl acetate (100 mL*3) and then the organic phase was washed by brine (200 mL*2) and dried over anhydrous sodium sulfate, then filtered and concentrated. The residue was purified by column chromatography to give intermediate 7E (yellow solid, 9.60 g 66.62% yield). LCMS (ESI) m/z: 574.9 (M+1). 1HNMR (400 MHz, DMSO-d6) δ ppm 1.09-1.27 (m, 2H) 1.41 (s, 9H) 1.77 (br d, J=11.13 Hz, 2H) 1.90-2.10 (m, 1H) 2.62-2.91 (m, 2H) 3.87-4.14 (m, 4H) 5.16-5.30 (m, 2H) 7.39-7.52 (m, 2H) 7.76 (dd, J=9.66, 2.45 Hz, 1H) 8.14-8.19 (m, 1H) 8.24 (d, J=7.58 Hz, 1H) 8.28 (s, 1H) 8.65 (s, 2H)

Step F:

Under nitrogen atmosphere, a mixed solution of intermediate 7F (200.00 mg, 348.77 mmol), 4,4,5,5-tetramethyl-2-(4,4,5,5-tetramethyl-1,3,2-dioxaborolane-2-yl)-1,3,2-dioxaborolane (92.99 mg, 366.21 mmol). Pd(dppf)Cl$_2$ (25.52 mg, 34.88 μmol) and potassium acetate (102.68 mg, 1.05 mmol) in 1,4-dioxane (10.00 mL) was stirred at 70° C. for 2 hours to give a solution of intermediate 7F in dioxane, which was used directly for the next step without further purification.

Step G:

Under nitrogen atmosphere, a mixed solution of intermediate 7F in dioxane solution (210.00 mg, 338.43 μmol), 2-bromopyridin-4-carbonitrile (185.81 mg, 1.02 mmol), Pd(dppf)Cl$_2$—CH$_2$Cl$_2$ (55.28 mg, 67.69 μmol) and potassium carbonate (93.55 mg, 676.86 μmol) in 1,4-dioxane (10.00 mL) and water (2.00 mL) was stirred at 80° C. for 3 hours. The reaction solution was then cooled to room temperature, filtered and concentrated. The residue was dissolved by adding water (50 mL) and extracted with ethyl acetate (30 mL*3). Then organic phases were combined, washed with brine (30 ml*2), dried over anhydrous sodium sulfate, followed by filtration and concentration. The residue was purified by preparative thin layer chromatography to give intermediate 7G (yellow solid, 50.00 mg, 24.76% yield). LCMS (ESI) m/z: 619.2 (M+23).

Step H:

Under nitrogen atmosphere, trifluoroacetic acid (4.62 g, 40.52 mmol, 3.00 mL) was added into a solution of intermediate 7G (50.00 mg, 83.80 μmol) in dichloromethane (10.00 mL) at 0° C. The reaction solution was stirred at 25° C. for 1 hour, then concentrated to obtain intermediate 7H (brownish black oily liquid, 60.00 mg, 100% yield, trifluoroacetate), which was used for the next step directly without further purification. LCMS (ESI) m/z: 497.2 (M+1).

Step I:

Under nitrogen atmosphere, formaldehyde (40.87 mg, 503.50 μmol, 37.50 μL, 37% aqueous solution) and sodium triacetoxyborohydride (64.03 mg, 302.10 μmol) were added into a solution of intermediate 7H (50.00 mg, 100.70 μmol) in dichloromethane (5.00 mL) at 0° C. The reaction solution was left at 25° C. for 16 hours, then concentrated. The residue was purified by preparative HPLC to obtain embodiment 7 (21.70 mg, 38.48% yield, formate). LCMS (ESI) m/z: 511.1 (M+1). 1HNMR (400 MHz, DMSO-d6) δ ppm 1.27-1.43 (m, 2H) 1.77 (br d, J=9.78 Hz, 3H) 1.99 (br t, J=11.43 Hz, 2H) 2.22 (s, 3H) 2.85 (br d, J=11.37 Hz, 2H) 4.05 (d, J=5.99 Hz, 2H) 5.39 (s, 2H) 7.50 (d, J=5.01 Hz, 2H) 7.75 (dd, J=5.01, 1.22 Hz, 1H) 8.18-8.26 (m, 2H) 8.28 (s, 1H) 8.33 (s, 1H) 8.40 (s, 1H) 8.64 (s, 2H) 8.78 (d, J=1.34 Hz, 1H) 8.82 (d, J=5.01 Hz, 1H)

Embodiment 8 (8-1 and 8-2)

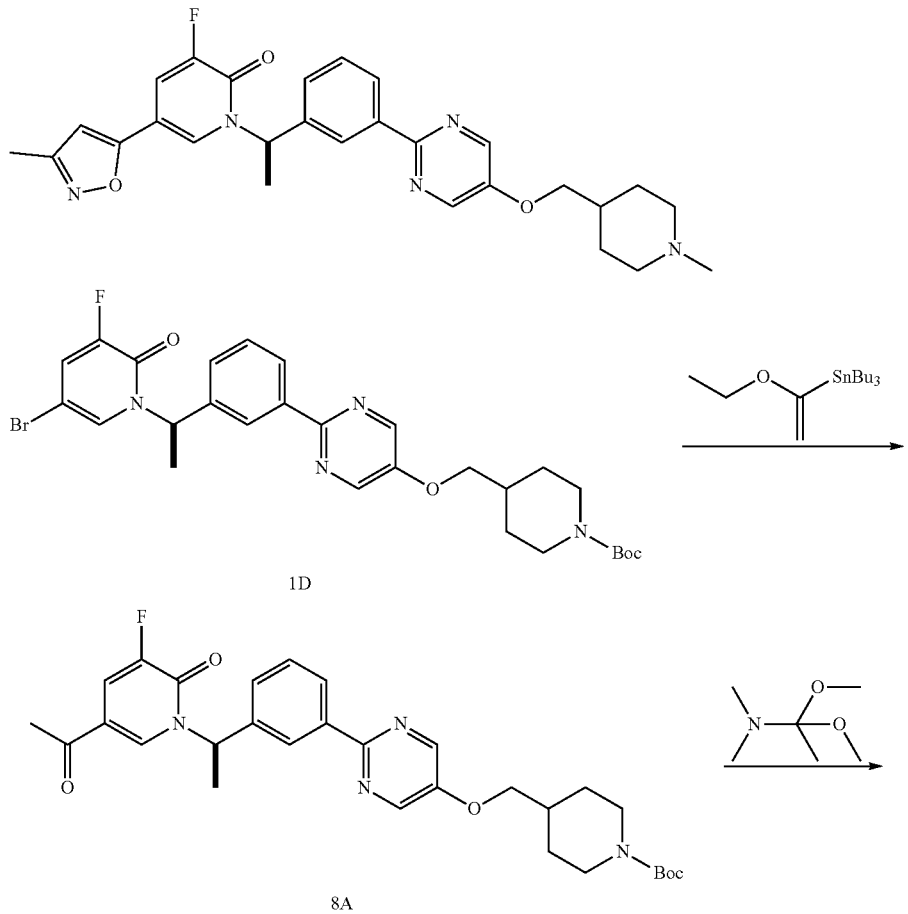

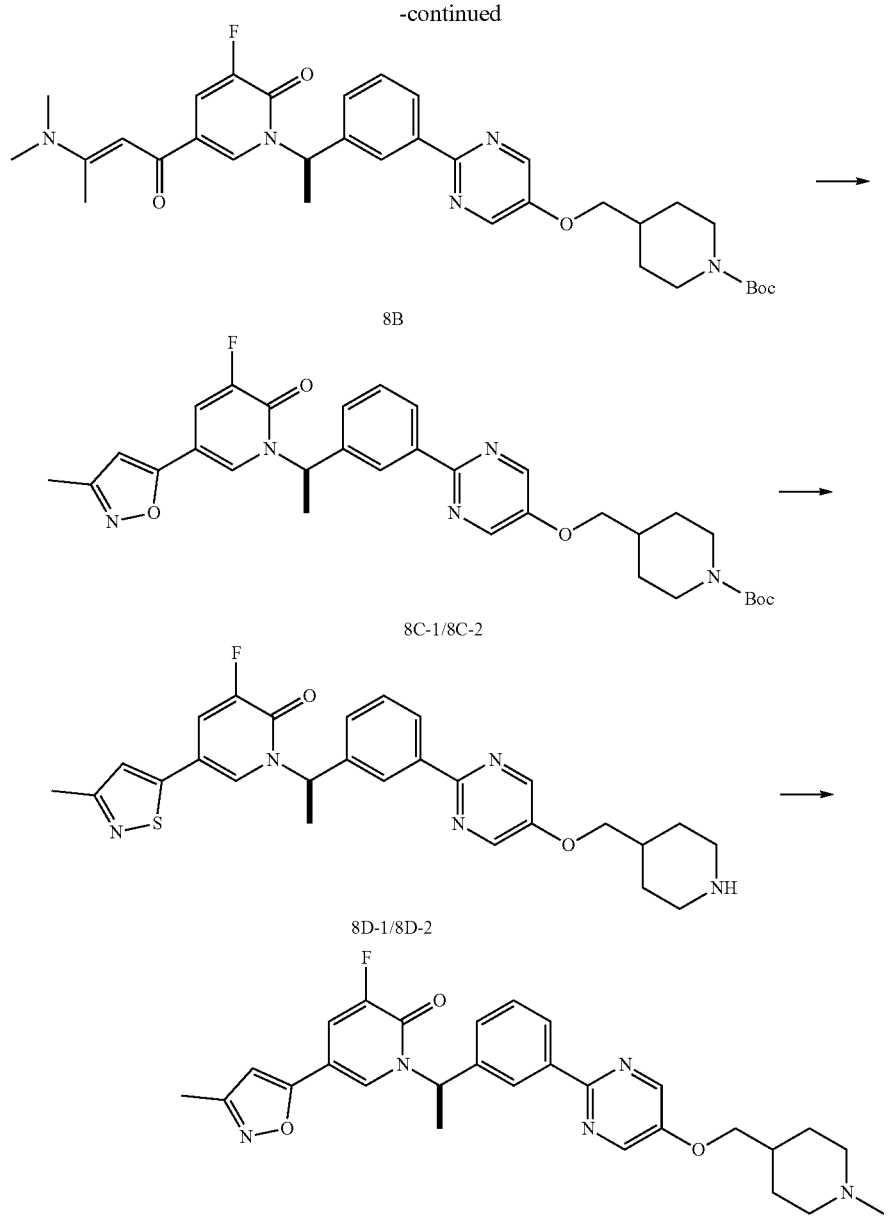

8B 8C-1/8C-2

8D-1/8D-2

Embodiment8(8-1/8-2)

Step A:

Under nitrogen atmosphere, a solution of intermediate 1D (1.50 g, 2.55 μmol), tributyl(1-ethoxyethylene)tin (1.14 g, 3.16 mmol, 1.07 mL) and Pd(dppf)Cl$_2$ (358.43 mg, 510.66 μmol) in toluene (10.00 mL) was stirred at 100° C. for 3 hours. Hydrochloric acid (10.21 mL, 1 N aqueous solution) was added into the reaction solution after the solution was cooled to room temperature and then the solution was stirred at 25° C. for 1 hour, filtered and concentrated. The residue was purified by column chromatography to give intermediate 8A (yellow oily liquid, 1.13 g, 80.48% yield). LCMS (ESI) m/z: 573.1 (M+23). 1HNMR (400 MHz, CHLOROFORM-d) δ ppm 1.50 (s, 9H) 1.89 (d, J=7.03 Hz, 6H) 1.98-2.10 (m, 2H) 2.31 (s, 3H) 2.72-2.86 (m, 2H) 3.98 (d, J=6.27 Hz, 2H) 4.12-4.31 (m, 2H) 6.54 (q, J=7.28 Hz, 1H) 7.42 (br d, J=7.65 Hz, 1H) 7.61 (dd, J=9.66, 2.26 Hz, 1H) 7.65-7.74 (m, 1H) 7.84 (d, J=1.38 Hz, 1H) 8.38 (d, J=7.78 Hz, 1H) 8.42 (s, 1H) 8.47 (s, 2H)

Step B:

Under nitrogen atmosphere, a solution of intermediate 8A (1.13 g, 2.05 mmol) in 1,1-dimethoxy-N,N-dimethyl-ethane (5.00 mL) was stirred at 120° C. for 3 hours. Then the reaction solution was cooled to room temperature and concentrated to dryness to obtain the intermediate 8B (brownish black oily liquid, 1.27 g, 100% yield), which was used directly for next step without further purification. LCMS (ESI) m/z: 620.1 (M+1).

Step C:

Under nitrogen atmosphere, hydroxylamine (213.61 mg, 3.08 mmol, hydrochloride salt) was added into a solution of intermediate 8B (1.27 g, 2.05 mmol) in ethanol (20.00 mL). The mixture was left at 80° C. for 16 hours, then concentrated. The residue was purified by preparative HPLC, the racemates were separated by preparative SFC (column: AS (250 mm*30 mm, 10 um); phase mobile: [0.1% NH$_3$—H$_2$O EtOH]: B %: 0%-55%, 5.2 min; 150 minmin) to intermediate 8C-1 (white solid, 380.00 mg, 31.44% yield, 100% ee value, Rt=2.431 min) and intermediate 8C-2 (white solid, 350.00 mg, 38.95% yield, 100% ee value, Rt=3.299 min). LCMS (ESI) m/z: 590.4 (M+1). 1HNMR (intermediate 8C-1) (400 MHz, CHLOROFORM-d) δ ppm 1.31-1.38 (m, 2H) 1.50 (s, 9H) 1.82-1.94 (m, 5H) 1.97-2.12 (m, 1H) 2.29 (s, 3H) 2.79 (br t, J=12.23 Hz, 2H) 3.98 (d, J=6.36 Hz, 2H) 4.21 (br s, 2H) 6.06 (s, 1H) 6.59 (d, J=6.97 Hz, 1H) 7.33 (dd, J=9.41, 2.20 Hz, 1H) 7.40-7.46 (m, 1H) 7.48-7.55 (m, 1H) 7.56-7.62 (m, 1H) 8.36 (d, J=7.70 Hz, 1H) 8.43 (s, 1H) 8.47 (s, 2H).

1HNMR (intermediate 8C-2) (400 MHz, CHLOROFORM-d) δ ppm 1.30-1.37 (m, 2H) 1.49 (s, 9H) 1.81-1.94 (m, 5H) 1.96-2.10 (m, 1H) 2.29 (s, 3H) 2.79 (br t, J=12.10 Hz, 2H) 3.98 (d, J=6.24 Hz, 2H) 4.20 (br s, 2H) 6.06 (s, 1H) 6.59 (q, J=7.05 Hz, 1H) 7.33 (dd, J=9.29, 2.20 Hz, 1H) 7.41-7.46 (m, 1H) 7.48-7.54 (m, 1H) 7.59 (d, J=1.59 Hz, 1H) 8.36 (d, J=7.82 Hz, 1H) 8.42 (s, 1H) 8.47 (s, 2H)

Step D:

Intermediates 8D-1, 8D-2 were prepared according to the preparation method of intermediate 1G.

Step E:

Embodiments 8-1, 8-2 were prepared according to the preparation method of embodiment 1.

Embodiment 8-1

LCMS (ESI) m/z: 504.1 (M+1).
1HNMR (400 MHz, DMSO-d6) δ ppm 1.54-1.72 (m, 2H) 1.85-2.13 (m, 6H) 2.24 (s, 3H) 2.69-2.80 (m, 3H) 2.86-3.16 (m, 2H) 3.19-3.52 (m, 2H) 4.09 (d, J=6.27 Hz, 2H) 6.29 (q, J=7.07 Hz, 1H) 6.78 (s, 1H) 7.47-7.60 (m, 2H) 7.92 (dd, J=10.42, 2.13 Hz, 1H) 8.08 (s, 1H) 8.21-8.35 (m, 2H) 8.62-8.75 (m, 2H) 10.37-10.80 (m, 1H)

Embodiments 8-2

LCMS (ESI) m/z: 504.1 (M+1).
1HNMR (400 MHz, DMSO-d6) δ ppm 1.57-1.74 (m, 2H) 1.81-2.12 (m, 6H) 2.23 (s, 3H) 2.62-2.79 (m, 3H) 2.86-3.05 (m, 2H) 3.41 (br d, J=11.92 Hz, 2H) 4.09 (d, J=6.27 Hz, 2H) 6.29 (q, J=6.99 Hz, 1H) 6.79 (s, 1H) 7.53 (d, J=5.02 Hz, 2H) 7.92 (dd, J=10.48, 2.07 Hz, 1H) 8.08 (s, 1H) 8.20-8.34 (m, 2H) 8.61-8.73 (m, 2H) 10.75 (br s, 1H)

Embodiment 9

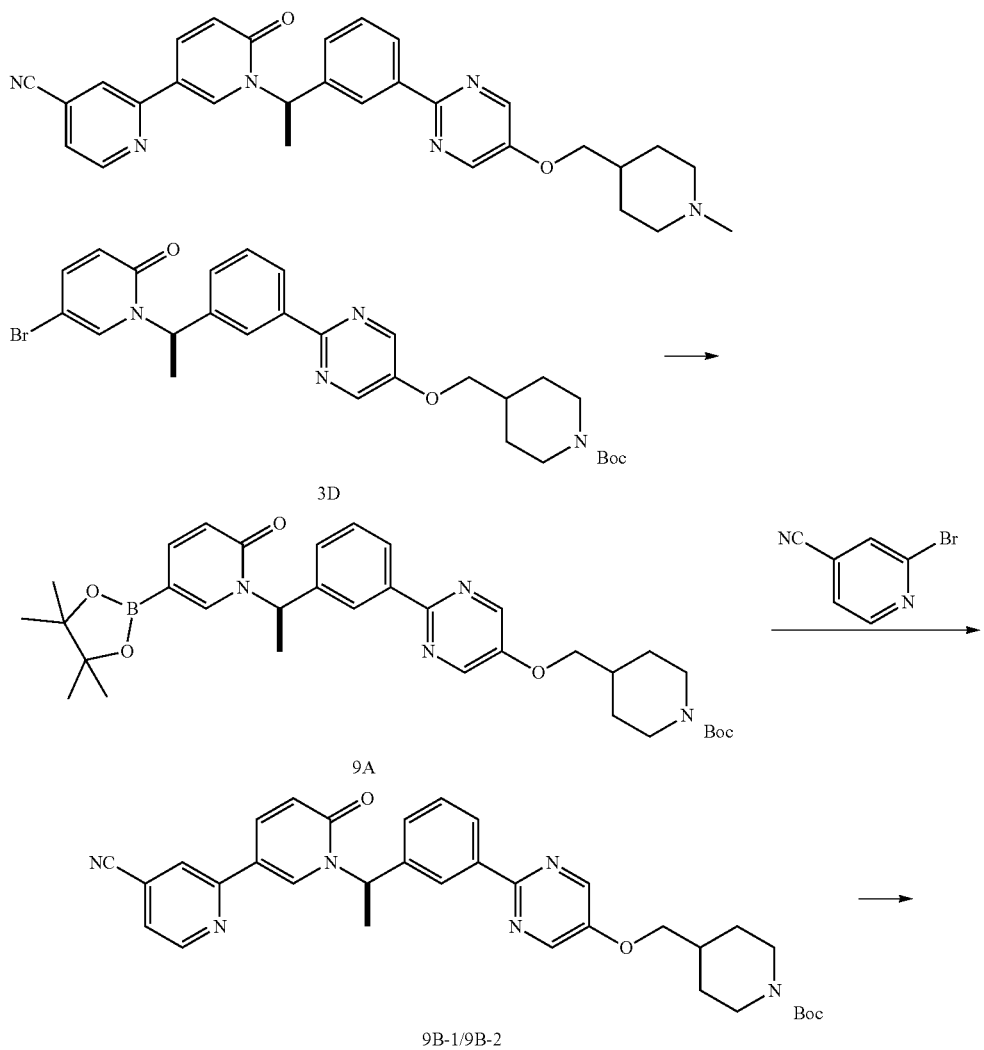

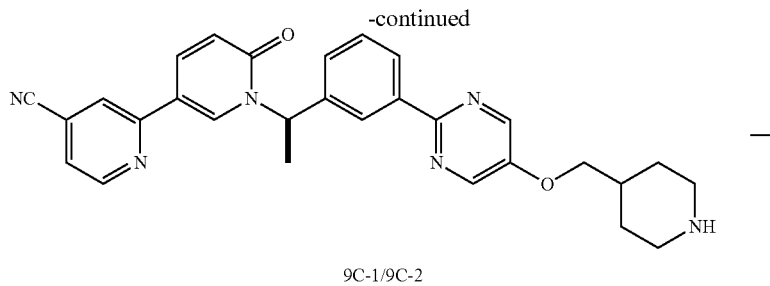

9C-1/9C-2

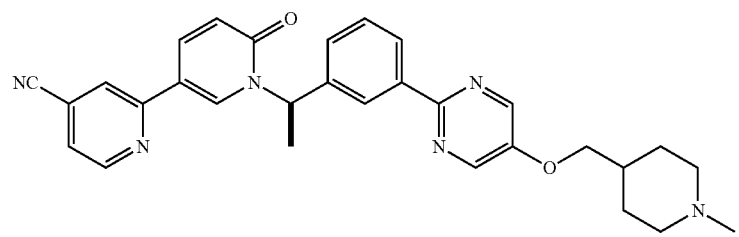

Embodiment 9(9-1/9-2)

Step A:
Under nitrogen atmosphere, a mixture of intermediate 3D (1.00 g, 1.76 mmol), 4,4,5,5-tetramethyl-(4,4,5,5-tetramethyl-1,3,2-dioxaborolane-2-yl)-1,3,2-dioxaborolane (469.28 mg, 1.85 mmol), Pd(dppf)Cl₂ (128.78 mg, 176.00 μmol) and potassium acetate (518.17 mg, 5.28 mmol) in 1,4-dioxane (15.00 mL) was stirred at 80° C. for 2 hours, then intermediate 9A in dioxane was obtained and was used directly for the next step without further treatment.

Step B:
Under nitrogen atmosphere, a mixture of intermediate 9A (1.09 g, 1.77 mmol) in dioxane, 2-bromopyridine-4-carbonitrile (485.89 mg, 2.66 mmol), Pd(dppf)Cl₂.CH₂Cl₂ (289.09 mg, 354.00 μmol) and potassium carbonate (489.26 mg, 3.54 mmol) in 1,4-dioxane (20.00 mL) and water (4.00 mL) in solution was stirred at 80° C. for 3 hours. Then the reaction solution was cooled to room temperature, filtered and concentrated. The residue was purified by preparative thin layer chromatography, the racemates was separated by preparative SFC (column: AS (250 mm*30 mm, 10 um); phase mobile: [0.1% NH₃—H₂O EtOH]; B %: 55%-55%, 8.2 min; 100 minmin) to intermediate 9B-1 (yellow oily liquid, 200.00 mg, 100% ee value, 19.06% yield, Rt=2.973 min) and intermediate 9B-2 (yellow oily liquid, 200.00 mg, 100% ee value, 19.06% yield, Rt=3.605 min). LCMS (ESI) m/z: 593.1 (M+1).

Step C
Intermediate 9C-1, 9C-2 was prepared according to the preparation method of 1G.

Step D:
Embodiment 9-1, 9-2 was prepared according to the preparation method of embodiment 1.

Embodiment 9-1

LCMS (ESI) m/z: 507.1 (M+1). 1HNMR (400 MHz, DMSO-d6) δ ppm 1.29-1.45 (m, 2H) 1.80 (br d, J=10.54 Hz, 3H) 1.88 (d, J=7.28 Hz, 3H) 2.14 (br t, J=11.17 Hz, 2H) 2.30 (s, 3H) 2.94 (br d, J=11.29 Hz, 2H) 4.05 (d, J=6.02 Hz, 2H) 6.32 (d, J=7.15 Hz, 1H) 6.62 (d, J=-9.66 Hz, 1H) 7.46-7.55 (m, 2H) 7.69 (dd, J=5.02, 1.25 Hz, 1H) 8.19-8.26 (m, 3H) 8.27 (s, 1H) 8.43 (t, J=1.07 Hz, 1H) 8.49 (d, J=2.38 Hz, 1H) 8.64 (s, 2H) 8.77 (dd, J=5.02, 0.88 Hz, 1H)

Embodiment 9-2

LCMS (ESI) m/z: 507.1 (M+1). 1HNMR (400 MHz. DMSO-d6) δ ppm 1.27-1.46 (m, 2H) 1.81 (br d, J=10.54 Hz, 3H) 1.89 (d, J=7.28 Hz, 3H) 2.17 (br t, J=11.17 Hz, 2H) 2.31 (s, 3H) 2.96 (br d, J=11.29 Hz, 2H) 4.09 (d, J=6.02 Hz, 2H) 6.35 (d, J=7.15 Hz, 1H) 6.65 (d, J=9.66 Hz, 1H) 7.42-7.57 (m, 2H) 7.66 (dd, J=5.02, 1.25 Hz, 1H) 8.21-8.27 (m, 3H) 8.29 (s, 1H) 8.45 (t, J=1.07 Hz, 1H) 8.51 (d, J=2.38 Hz, 1H) 8.67 (s, 2H) 8.79 (dd, J=5.02, 0.88 Hz, 1H)

Embodiment 10

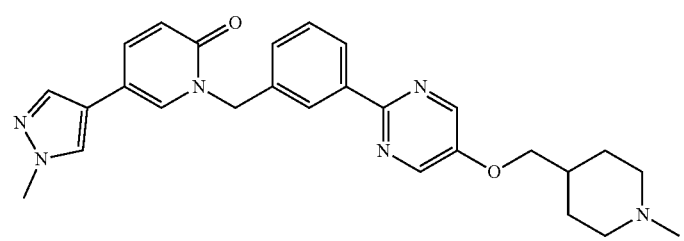

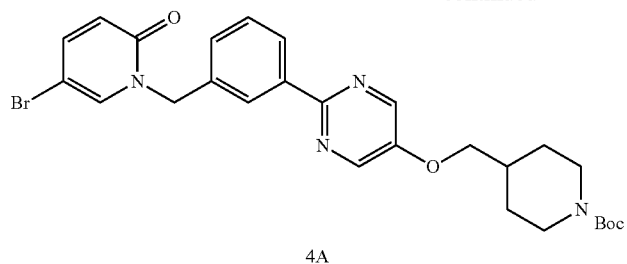

4A

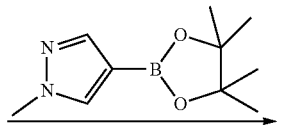

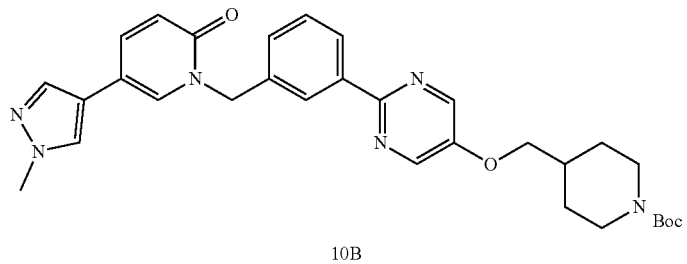

10B

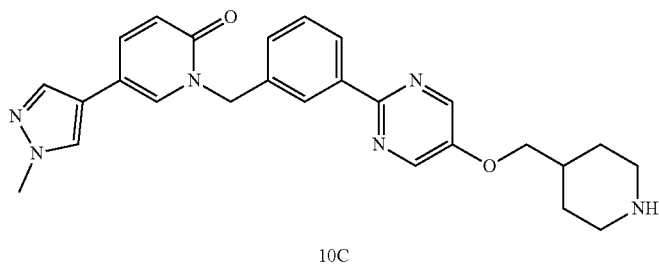

10C

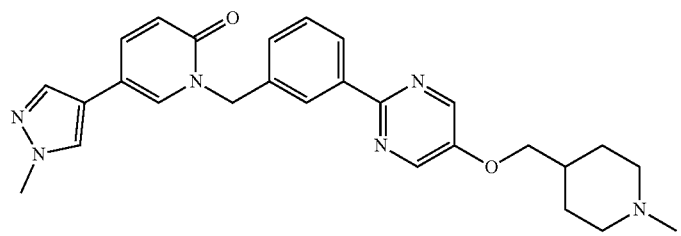

Embodiment 10

Step A:

Under nitrogen atmosphere, a mixture of intermediate 4A (200.00 mg, 346.53 μmol), 1-methyl-4-(4,4,5,5-tetramethyl-1,3,2-dioxaborolane-2-yl)pyrazole (108.15 mg, 519.80 μmol), Pd(dppf)Cl$_2$ (25.36 mg, 34.65 μmol) and sodium carbonate (110.19 mg, 1.04 mmol) in 1,4-dioxane (10.00 mL) was stirred at 80° C. for 2 hours, then the reaction solution was cooled to room temperature, filtered and concentrated. The residue was dissolved by adding water (60 mL) and then extracted with ethyl acetate (50 mL*3). Then organic phases were combined and washed with brine (80 mL*2), and dried over anhydrous sodium sulfate, filtered and concentrated. The residue was purified by preparative thin layer chromatography to give intermediate 10B (yellow oily liquid, 200.00 mg, 95.45% yield). LCMS (ESI) m/z: 557.3 (M+1).

Step B:

Intermediate 10C was prepared according to the preparation method of intermediate 1G.

Step C:

Embodiment 10 was prepared according to the preparation method of embodiment 1. LCMS (ESI) m/z: 471.2 (M+1). 1HNMR (400 MHz, METHANOL-d4): 1.63-1.80 (m, 2H) 2.09-2.25 (m, 3H) 2.88 (s, 3H) 3.05 (t, J=12.17 Hz, 2H) 3.55 (d, J=12.67 Hz, 2H) 3.91 (s, 3H) 4.12 (d, J=5.90 Hz, 2H) 5.34 (s, 2H) 6.67 (d, J=9.41 Hz, 1H) 7.42-7.51 (m, 2H) 7.75 (s, 1H) 7.81 (dd, J=9.35, 2.57 Hz, 1H) 7.88 (s, 1H) 8.05 (d, J=2.38 Hz, 1H) 8.25-8.29 (m, 1H) 8.33 (s, 1H) 8.47 (s, 1H) 8.55 (s, 2H).

Embodiment 11
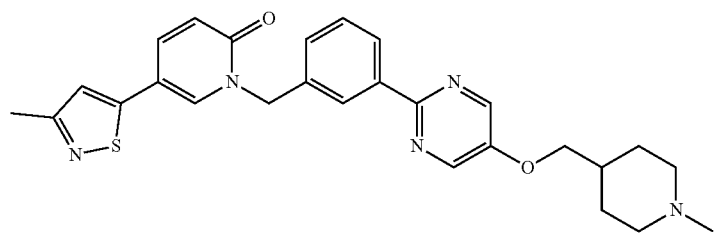
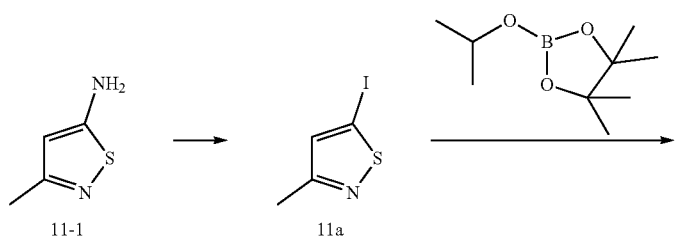
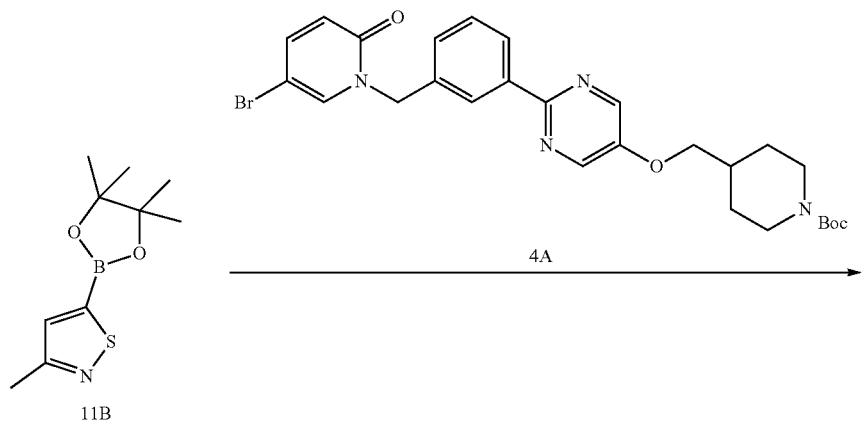
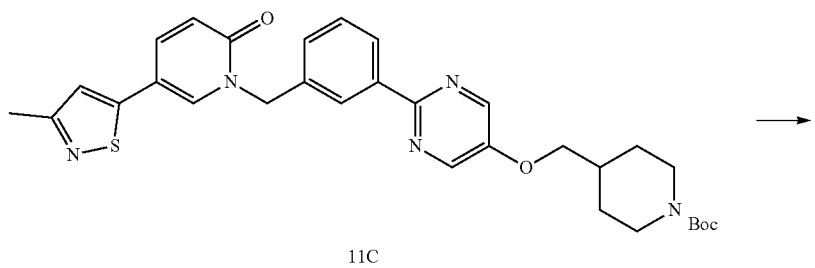
11C
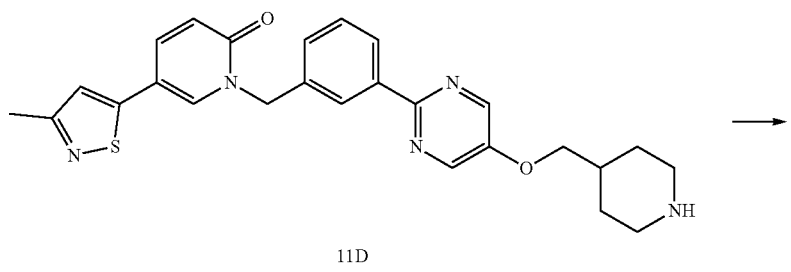
11D

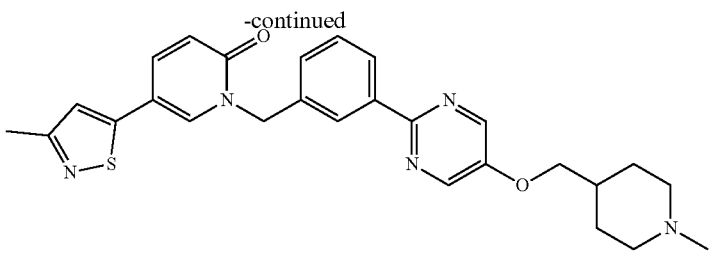

Embodiment 11

Step A:
Under nitrogen atmosphere, a solution of sodium nitrite (2.52 g, 36.54 mmol) in water (50 mL) was added dropwise into a mixed solution of 3-methyisothiazol-5-amine (5.00 g, 33.19 mmol, hydrochloride salt) in water (14.00 mL) and sulfuric acid (10.00 mL, 98% purity) at 0° C. The reaction solution was stirred at 0° C. for 1 hour, then a solution of potassium iodide (6.06 g, 36.51 mmol) in water (35 mL) was added and the solution was left at 80° C. for 1 hour for reaction. The reaction solution was cooled to room temperature, diluted with water (100 mL) and extracted with dichloromethane (50 mL*2). Then the organic phases were combined and washed with brine (25 mL*2), dried over anhydrous sodium sulfate, filtered and concentrated. The residue was purified by column chromatography to give intermediate 11A (yellow solid, 4.00 g, 53.55% yield). LCMS (ESI) m/z: 225.9 (M+1). 1HNMR (400 MHz, CHLOROFORM-d) δ ppm 2.39-2.48 (m, 3H) 7.04-7.13 (m, 1H).

Step B:
Under nitrogen atmosphere, isopropylamagnesium chloride-lithium chloride complex (3.66 mL, 1.3 M tetrahydrofuran solution) was added dropwise into a solution of intermediate 11A (1.00 g, 4.44 mmol) and 2-isopropoxy-4,4,5,5-1,3,2-dioxaborolane (850 mg, 4.57 mmol) in tetrahydrofiran (5.00 mL) at −25° C. The reaction solution was stirred at −25° C. for 0.5 hour. After the reaction, the solution was quenched by dripping into a solution of acetic acid (0.24 mL) in tetrahydrofuran (0.67 mL), then petroleum ether (48 mL) and tert-butyl methyl ether (24 mL) were added into the reaction solution. After filtration, tert-butyl methyl ether (32 mL) was added into filtrate, then the filtrate was again filtered and concentrated to give intermediate 11B (yellow oily liquid, 512 mg, 51.22% yield) which was used for the next step directly without further purification. 1HNMR (400 MHz, CHLOROFORM-d) δ ppm 1.28 (s, 12H) 2.46-2.48 (m, 3H) 7.31 (s, 1H).

Step C:
Under nitrogen atmosphere, a mixture of intermediate 11B (283.69 mg, 1.26 mmol), intermediate 4A (500.00 mg, 900.15 μmol), 1,1-di(tert-butylphosphino)ferrocene palladium chloride (58.67 mg, 90.02 μmol) and potassium phosphate trihydrate (479.44 mg, 1.80 mmol) in tetrahydrofuran (5.00 mL) and water (1.00 mL) was stirred at 65° C. for 12 hours. Then the reaction solution was cooled to room temperature, filtered and concentrated. After the residue was dissolved in water (50 mL) and extracted with ethyl acetate (100 mL*2), the organic phases were combined and washed with brine (50 mL*2), dried over anhydrous sodium sulfate, filtered and concentrated. The residue was purified by preparative thin layer chromatography to give intermediate 11C (yellow solid, 266.00 mg, 51.51% yield). LCMS (ESI) m/z: 574.2 (M+1). 1HNMR (400 MHz, CHLOROFORM-d) δ ppm 1.27-1.34 (m, 6H) 1.60-1.64 (m, 10H) 1.60-1.65 (m, 10H) 1.83-1.91 (m, 2H) 1.95 (s, 1H) 2.46-2.52 (m, 3H) 3.95-4.01 (m, 2H) 5.28-5.31 (m, 2H) 6.71-6.77 (m, 1H) 6.94-6.97 (m, 1H) 7.39-7.56 (m, 3H) 7.63-7.68 (m, 1H) 8.37 (s, 2H) 8.47 (s, 2H).

Step D:
Intermediate 11D was prepared according to the preparation method of intermediate 1F.
LCMS (ESI) m/z: 474.2 (M+1).

Step E:
Embodiment 11 was prepared according to the preparation method of embodiment 1.
LCMS (ESI) m/z: 488.2 (M+1). 1HNMR (400 MHz, DMSO-d6) δ ppm 1.37 (br d, J=10.54 Hz, 2H) 1.79 (br d, J=10.04 Hz, 3H) 2.11 (br s, 2H) 2.26-2.31 (m, 3H) 2.40-2.44 (m, 3H) 2.89-2.97 (m, 2H) 4.01-4.09 (m, 2H) 5.25 (s, 2H) 6.57 (d, J=9.41 Hz, 1H) 7.45 (d, J=1.80 Hz, 3H) 7.79 (dd, J=9.41, 2.64 Hz, 1H) 8.20-8.26 (m, 2H) 8.29 (s, 1H) 8.53-8.56 (m, 1H) 8.62-8.66 (m, 2H).

Embodiment 12

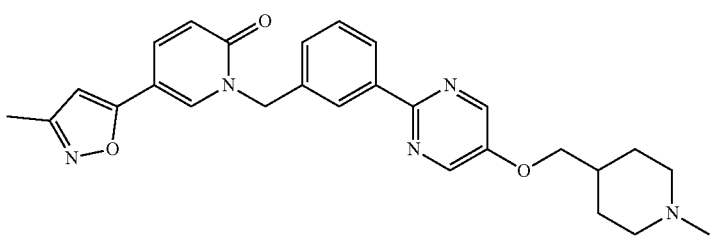

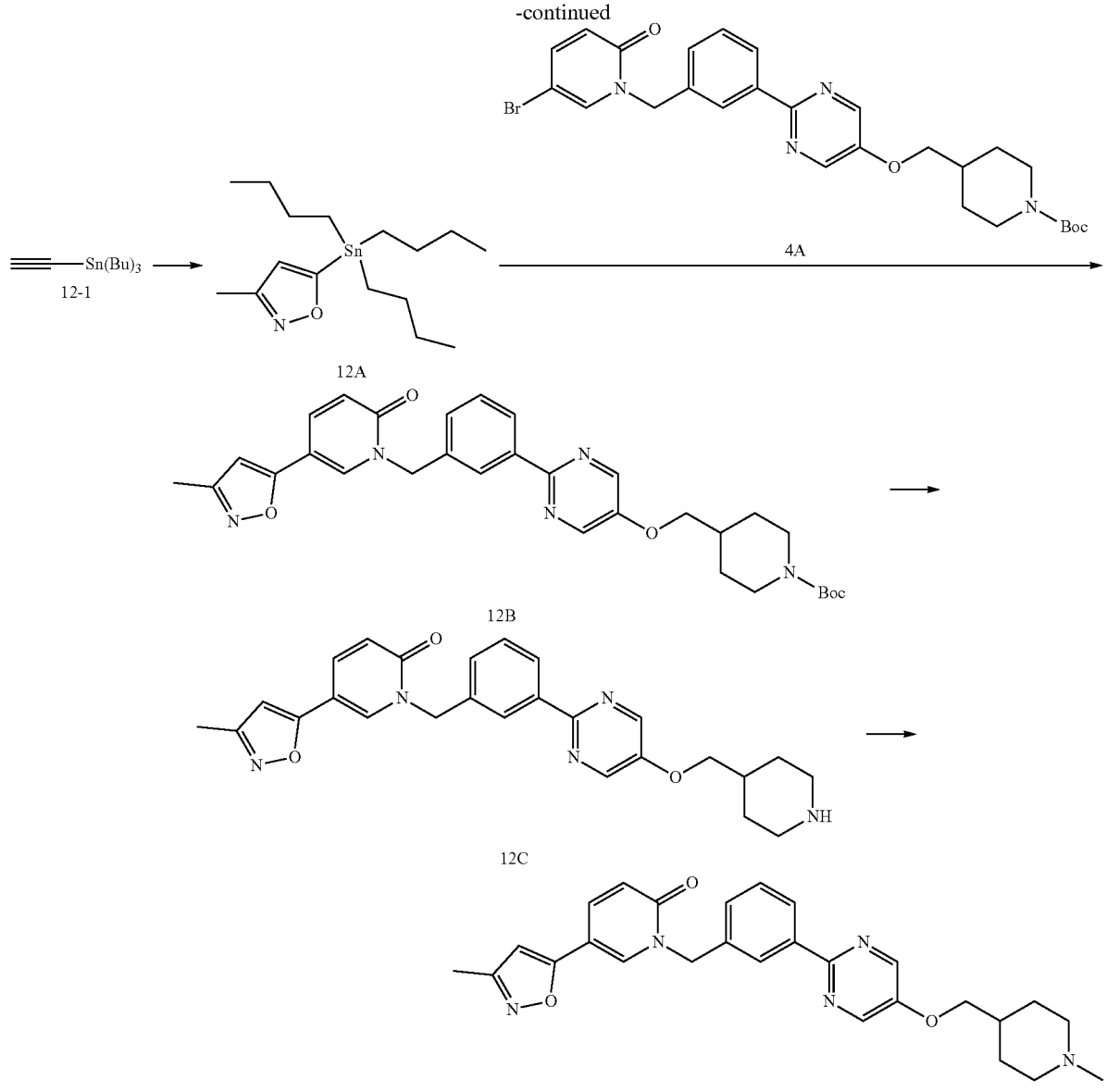

Embodiment 12

Step A:

Triethylamine (32.08 mg, 317.00 μmol, 43.94 μL) was added into a solution of phenyl isocyanate (830.74 mg, 6.97 mmol) in nitroethane (261.77 mg, 3.49 mmol, 249.30 L) and the reaction solution was stirred at 50° C. for 30 minutes, then a solution of tributyl(ethynyl)stannane (1.00 g, 3.17 mmol) in toluene (8.00 mL) was added into the reaction solution, followed by stirring at 50° C. for 5 hours. Thin layer chromatography was used to detect the completion of the reaction. Then water (100 mL) was added into the solution, which then was extracted with ethyl acetate (100 mL). The organic phase was then washed with brine (50 mL) and dried over anhydrous sodium sulfate, filtered and concentrated with a rotary evaporator. The residue was purified by column chromatography to give intermediate 12A (yellow oily liquid, 700.00 mg, 42.13% yield). LCMS (ESI) m/z: 373.14 (M+1). 1H NMR (400 MHz, CHLOROFORM-d) δ ppm 0.82-0.85 (m, 9H) 0.97-1.11 (m, 6H) 1.20-1.34 (m, 12H) 1.49-1.52 (m, 3H) 7.18-7.20 (m, 1H).

Step B:

Intermediate 12A (200 mg, 348.77 μmol) and Pd(PPh$_3$)$_2$Cl$_2$ (25.27 mg, 36.01 μmol) were added into a solution of intermediate 4A (200.00 mg, 360.06 μmol) in dioxane (4.00 mL) at 20° C., then heated to 100° C. and stirred for 12 hours under nitrogen atmosphere. Thin layer chromatography was used to detect the completion of the reaction. Then water (50 mL) was added into the reaction solution and the solution was extracted with ethyl acetate (50 mL*2). The organic phase was washed with brine (50 mL), dried over anhydrous sodium sulfate, filtered and concentrated with rotary evaporator. The residue was purified by column chromatography to give intermediate 12B (yellow solid, 110.00 mg, 42.18% yield). LCMS (ESI) m/z: 557.26 (M+1). 1H NMR (400 MHz, CHLOROFORM-d) δ ppm 1.21-1.31 (m, 4H) 1.40 (s, 9H) 1.72-1.81 (m, 2H) 1.89-1.98 (m, 1H) 2.22 (s, 3H) 2.70 (br s, 2H) 3.88 (d, J=6.36 Hz, 2H) 5.21 (s, 2H) 6.02 (s, 1H) 6.63 (d, J=9.54 Hz, 1H) 7.33-7.37 (m, 1H) 7.50 (dd, J=9.54, 2.57 Hz, 1H) 7.57-7.64 (m, 1H) 7.83 (d, J=2.32 Hz, 1H) 8.23-8.31 (m, 2H) 8.38 (s, 2H).

Step C:

Intermediate 12C was prepared according to the preparation method of intermediate 1G. LCMS (ESI) m/z: 457.21 (M+1).

Step D:

Embodiment 12 was prepared according to the preparation method of embodiment 1. LCMS (ESI) m % z: 471.23 (M+1). 1H NMR (400 MHz, DMSO-d6) δ ppm 1.14-1.21 (m, 2H) 1.49 (br s, 2H) 1.79-1.95 (m, 3H) 1.99 (s, 2H) 2.24 (s, 3H) 2.38-2.38 (m, 1H) 2.46 (s, 3H) 3.12 (br d, J=10.92 Hz, 2H) 5.29 (s, 2H) 6.65 (s, 1H) 7.47 (br s, 1H) 7.82-7.90 (m, 1H) 8.29 (br s, 2H) 8.63 (s, 2H)

Assay 1: Binding Activity of c-MET Enzyme Assay

Reagents and Consumables:

cMET (invitrogen PV3143)
Tracer 236 (Lot Number: 10815978)
Eu-Anti-His AB (MAb Anti 6HIS-K)
PerkinElmer corporation Envison detection 665 nm and 615 nm
384-well plate_checkerboard (PerkinElmer #6007299)

Experimental Principle:

The present experiment utilized the LanthaScreen™ Eu Kinase Binding Assay, as shown in FIG. 1, detection of Alexa Fluor conjugates or kinase combines tracer agent was done by adding Eu labelled antibody. The binding of tracer agent and antibody and kinase leaded to high FRET standard, while using kinase inhibitor instead of tracer agent would lead to loss of FRET.

Experimental Method:

1) The antibody Eu-Anti-His AB, enzyme cMET, tracer agent Tracer236 were diluted.

2) Preparation of the compound: 10 mM test compound and reference compound were diluted by 100% DMSO to 0.667 mM, then fully automated microplate pretreatment system ECHO was used for a 3-time dilution with 8 concentration gradients. Double duplicate wells were set and each of them 75 nL.

3) The mixture of 7.5 μL antibody (1/375 nM) and kinase (10 nM) was added to the compound plate, followed by addition of 7.5 μL Tracer (60 nM). Final concentration: cMET: 5 nM, Tracer 236: 30 nM, Eu-Anti-His AB (MAb Anti 6HIS-K): 1/750 nM.

4) After 60 mins of incubation at 4° C., Envision readings were performed with a multi-labelled microplate reader (data analysis of 665 nm/615 mm signal values with Prism 5; Ex excitation light: Laser mirror 446, Em excitation light; 615 and 665 nM.

Experimental result: See Table 1.

Conclusion: the compounds of the present invention have a relatively strong inhibitory effect on the c-MET enzyme.

TABLE 1

| Test compound | c-MET IC$_{50}$ (nM) |
| --- | --- |
| Embodiment 1-2 | 1.09 |
| Embodiment 2-2 | 9.33 |
| Embodiment 4 | 6.16 |
| Embodiment 5 | 2.90 |
| Embodiment 6 | 4.37 |
| Embodiment 7 | 15.50 |
| Embodiment 8-2 | 3.79 |

TABLE 1-continued

| Test compound | c-MET IC$_{50}$ (nM) |
| --- | --- |
| Embodiment 10 | 69.50 |
| Embodiment 11 | 5.00 |

Assay 2: Inhibitory Effect Assay on Proliferation

Reagents and Consumables:

1) Cell culture: DMEM cell medium, fetal bovine serum, DPBS
2) Cell line: MHCC97-H
3) Detection reagent: live cell detection kit CellTiter-Glo
4) Other major consumables and reagents: compound dilution plate, intermediate plate, test plate, DMSO Experimental Principle:

The amount of ATP directly reflects the number of cells and the state of the cells, thus the number of living cells could be directly detected by quantitatively measuring ATP. The live cell assay kit contains luciferase and its substrate. With the presence of ATP, a stable optical signal would be emitted by the luciferase catalyzed substrate. Thus the amount of ATP in the cell could be determined by detecting the intensity of the signal. The light signal was proportional to the amount of ATP in the cell, while the ATP was positively correlated with the number of living cells, so that the proliferation in the cell could be detected. The assay plate used was analyzed by Envision from PE Corporation.

Experimental Method:

1. Preparation of the Cell Plates

MHCC97-H cells were seeded separately into 384-well plates, each of the well contains 500 cells. The cell plates were placed and incubated in a carbon dioxide incubator overnight.

2. Preparation of the compound.

Echo was used for 4-time dilution and 9 concentration was prepared, ready for double duplicate wells assay.

3. Compound Treatment of Cells

The compounds were transferred to cell plates at a starting concentration of 10 μM. The cell plates were incubated in a carbon dioxide incubator for 3 days.

4. Detection

The Promegaer-Glo reagent was added into the cell plates and the plate was incubated at room temperature for 10 mins to stabilize the luminescence signal. PerkinElmer Envision multi-label analyzer was used for readings.

Experimental results: See Table 2:

Conclusion: the compounds of the present invention exhibit good inhibitory activity against MHCC97H cells.

TABLE 2

| Test compound | MHCC97H cell IC$_{50}$ (nM) |
| --- | --- |
| Embodiment 1 | 8.80 |
| Embodiment 2-2 | 13.80 |
| Embodiment 3-2 | 19.0 |
| Embodiment 4 | 72.90 |
| Embodiment 5 | 58.80 |
| Embodiment 6 | 32.90 |
| Embodiment 7 | 22.30 |
| Embodiment 9-2 | 22.10 |
| Embodiment 10 | 166.00 |
| Embodiment 11 | 93.80 |
| Embodiment 12 | 51.40 |

Assay 3: Pharmacodynamics Assay of MHCC97H Liver Cancer Cell Subcutaneous Xanograft Tumor Model Cell Culture:
MHCC97H cells were cultured in a single layer in-vitro. The culturing condition was RPMI1640 medium supplemented with 10% heat-inactivated fetal bovine serum, 1% penicillin-streptomycin double antibody under 37° C., 5% carbon dioxide. Digestion and passage treatment with trypsin-EDTA was done twice a week. When the cells are in the exponential growing phase, the cells were collected, counted and inoculated.

Animal:
BALB/c nude mice, male. 6-8 weeks old, weighting 18-22 g.

Tumor Inoculation:
0.2 mL of a cell suspension containing 5×10^6 MHCC97H was subcutaneously inoculated into the right back of each mouse. Drugs were administered by group after the average tumor volume reached approximately 172 mm³. The experimental grouping and administrational schedule are shown in the table below.

Aim of the assay: investigation of whether the tumor growth was inhibited, delayed or cured. The diameters of the tumor was measured twice a week using vernier calipers. The formula for calculating the tumor volume is V=0.5a×b2, and a and b represent the long and short diameters of the tumor respectively. The antitumor effect (TGI) of the compounds was evaluated by T-C (days) and T/C (%).

Experimental results: see in Table 3.

Conclusion: the compounds of the present invention exhibit better tumor inhibitory activity than Tepotinib in the pharmacodynamics assays of the subcutaneous xenograft tumor model of MHCC97H hepatoma cells.

TABLE 3

Evaluation of the anti-tumor efficacy of tested drugs on human liver cancer MHCC97H cell xenograft model (calculations based on the 24th day-tumor-volume after administration of drug)

| group | Tumor volume (mm³)[a] (24th day) | T/C (%) | TGI (%) | p value [b] |
|---|---|---|---|---|
| blank | 2059 ± 305 | — | — | — |
| (Tepotinib) | 255 ± 5 | 12.4 | 95.6 | <0.001 |
| Embodiment 1-2 | 153 ± 12 | 7.4 | 101.0 | <0.001 |
| Embodiment 8-2 | 161 ± 6 | 7.8 | 100.6 | <0.001 | remarks:
[a] average ± SEM.
[b] p value was calculated based on the volume of the tumor.

The compounds of the present invention have better metabolic stability than tepotinib. For example, the $t_{1/2}$ of liver particle metabolism in the three species of human, rat and mice of embodiment 1-2 are 62.1 min, 36.5 min and 49.1 min respectively. While under the same conditions for Tepotinib in the three species of human, rat and mice, the $t_{1/2}$ of liver particle metabolism are 48.3 min, 10.5 min and 12.4 min respectively. The compounds of the present invention have an extended half-time and action time on the target, an enhanced metabolic stability and more excellent inhibitory activity. The prolongation of half-time would keep the concentration in the blood for a longer time. Thus comparing to other medicament in the tumor treatment, the compounds would reduce the dose and interval between doses so that the patient compliance would be significantly improved.

Since when c-MET combined with HGF, it activated the MAPK, PI3K/AKT. CDc42-Rac1 and other pathways, leading to tumor cells survival and proliferation, thereby accelerated the tumor growth rate. Thus the pyridone compound as c-Met inhibitor has great application prospects in targeted therapeutic drugs such as liver cancer, non-small cell lung cancer and gastric cancer. Especially in treating liver cancer, this compound has a precise therapeutic effect on liver cancer with high expression of c-Met. Therefore, the pyridone compound as c-Met inhibitor in the present invention is expected to be a more therapeutically effective new drug than other similar products in view of its remarkable inhibitory activity in vivo and in vitro, as well as its good metabolic stability.

What is claimed is:

1. A compound represented by formula (I) or a pharmaceutically acceptable salt,

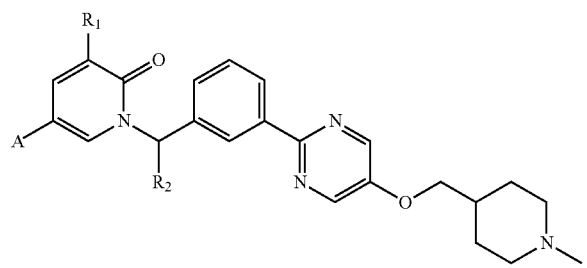

(I)

$R_1$ is selected from H or F;
$R_2$ is selected from H or $CH_3$;
while $R_2$ is not H, the configuration of the carbon atom bonded to $R_2$ is R or S;
A is selected from the group consisting of phenyl, pyridyl, pyrazolyl, isoxazolyl, isothiazolyl and thiazolyl, each of which is optionally substituted by 1, 2 or 3 $R_3$;
$R_3$ is selected from CN, halogen, C(=O)$NH_2$, or is selected from the group consisting of $C_{1-6}$ alkyl, $C_{1-6}$ heteroalkyl, and $C_{3-6}$ cycloalkyl, each of which is optionally substituted by 1, 2 or 3 $R_0$;
$R_0$ is selected from F, Cl, Br, I, OH, CN, $NH_2$, C(=O)$NH_2$, or is selected from the group consisting of $C_{1-3}$ alkyl and $C_{1-3}$ heteroalkyl, each of which is optionally substituted by 1, 2 or 3 R';
R' is selected from F, Cl, Br, I, CN, OH, $NH_2$, $CH_3$, $CH_3CH_2$, $CF_3$, $CHF_2$ or $CH_2F$;
the "hetero" in the $C_{1-3}$ heteroalkyl or $C_{1-6}$ heteroalkyl is selected from the group consisting of —O—, —C(=O)NR'—, —C(=O)NH—, —NR'—, and —NH—;
in any of the above cases, the number of the heteroatom or the heteroatomic group is independently selected from 1, 2 or 3.

2. The compound or the pharmaceutically acceptable salt as defined in claim 1, wherein, $R_0$ is selected from F, Cl, Br, I, OH, CN, $NH_2$, C(=O)$NH_2$, $CH_3$, $CH_3CH_2$, $CF_3$, $CHF_2$, $CH_2F$, $NH_2CH_2$, $(NH_2)_2CH$, $CH_3O$, $CH_3CH_2O$, $CH_3OCH_2$, $CH_3NH$ or $(CH_3)_2N$.

3. The compound or the pharmaceutically acceptable salt as defined in claim 1, wherein, $R_1$ is H.

4. The compound or the pharmaceutically acceptable salt as defined in claim 1, wherein, $R_1$ is F.

5. The compound or the pharmaceutically acceptable salt as defined in claim 1, wherein, $R_2$ is H.

6. The compound or the pharmaceutically acceptable salt as defined in claim 1, wherein, $R_2$ is $CH_3$.

7. The compound or the pharmaceutically acceptable salt as defined in claim 6, wherein, the configuration of the carbon atom bonded to $R_2$ is R.

8. The compound or the pharmaceutically acceptable salt as defined in claim 6, wherein, the configuration of the carbon atom bonded to $R_2$ is S.

9. The compound or the pharmaceutically acceptable salt as defined in claim 1, wherein, $R_3$ is selected from CN, halogen, C(=O)NH$_2$, or is selected from the group consisting of $C_{1-3}$ alkyl and $C_{1-3}$ heteroalkyl, each of which is optionally substituted by 1, 2 or 3 $R_0$.

10. The compound or the pharmaceutically acceptable salt as defined in claim 9, wherein, $R_3$ is selected from CN, F, Cl, Br, $CH_3$, $CH_3CH_2$, $CF_3$, $CHF_2$, $CH_2F$, $CH_3O$ or C(=O)NH$_2$.

11. The compound or the pharmaceutically acceptable salt as defined in claim 1, wherein, A is selected from the group consisting of

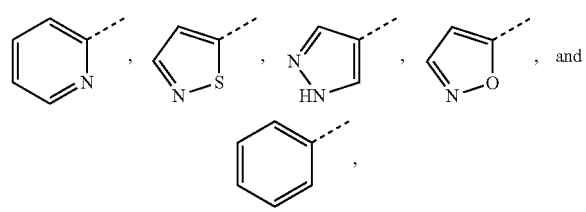

each of which is optionally substituted by 1, 2 or 3 $R_3$.

12. The compound or the pharmaceutically acceptable salt as defined in claim 11, wherein, A is selected from the group consisting of

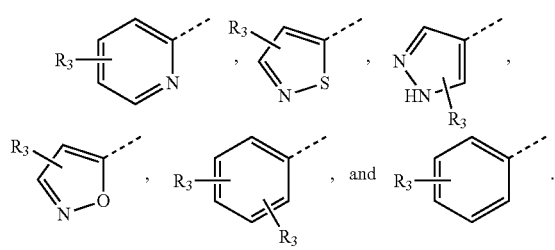

13. The compound or the pharmaceutically acceptable salt as defined in claim 12, wherein, A is selected from the group consisting of

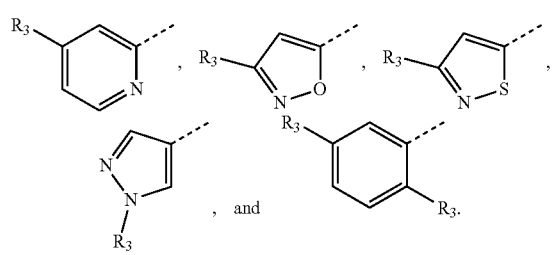

14. The compound or the pharmaceutically acceptable salt as defined in claim 10, wherein, A is selected from the group consisting of

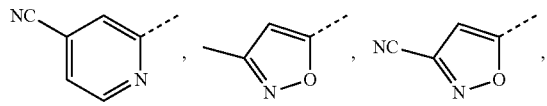

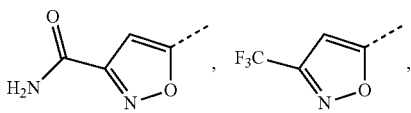

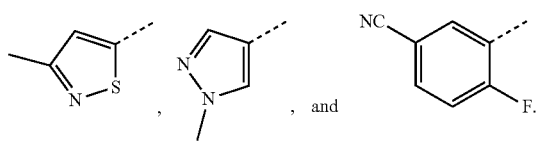

15. The compound as defined in claim 1 is selected from the group consisting of embodiment 1

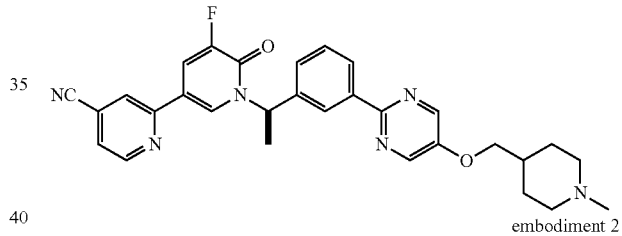

embodiment 2

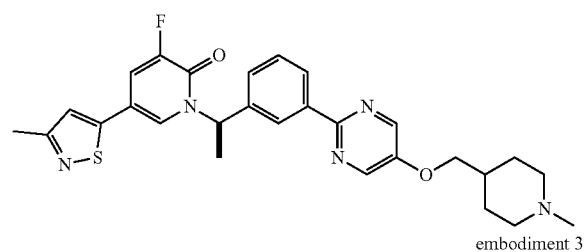

embodiment 3

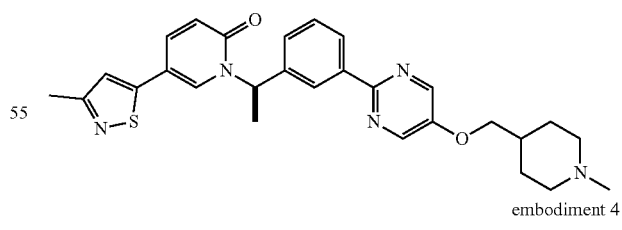

embodiment 4

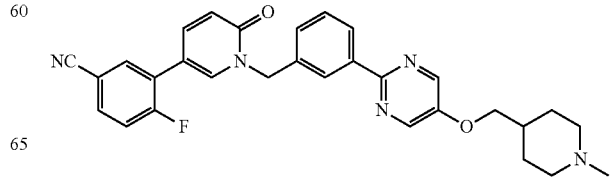

embodiment 5

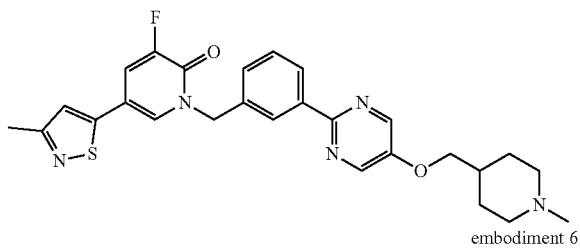

embodiment 6

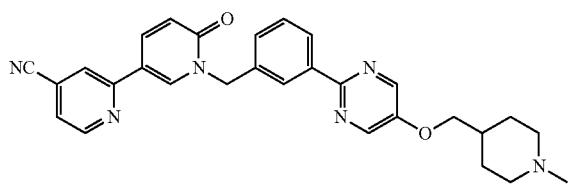

embodiment 7

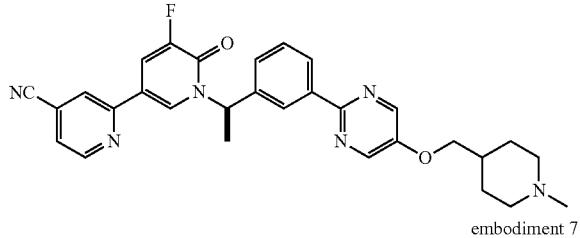

embodiment 8

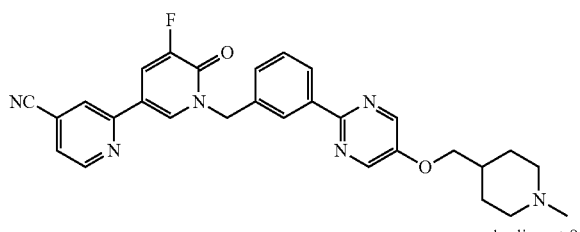

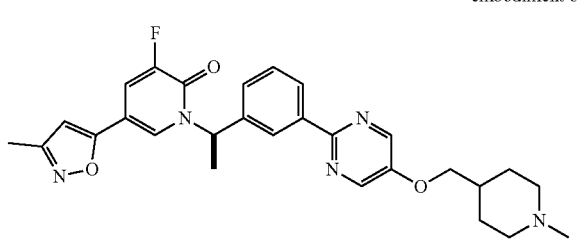

embodiment 9

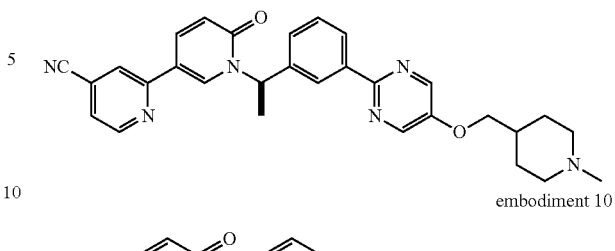

embodiment 10

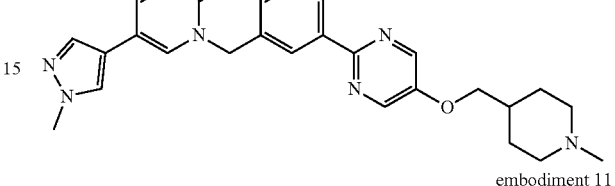

embodiment 11

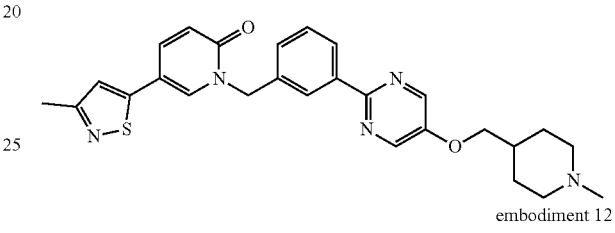

embodiment 12

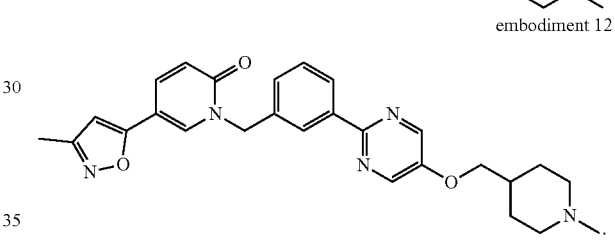

16. A pharmaceutical composition comprising a therapeutically effective amount of the compound or the pharmaceutically acceptable salt thereof as defined in claim 1, as well as a pharmaceutically acceptable carrier.

17. A method for treating tumor, comprising administering to a subject in need thereof the pharmaceutical composition as defined in claim 16, wherein the tumor is selected from liver cancer, non-small cell lung cancer, or gastric cancer.

\* \* \* \* \*